US007892735B2

(12) United States Patent
Brennan et al.

(10) Patent No.: US 7,892,735 B2
(45) Date of Patent: Feb. 22, 2011

(54) GENETIC MARKERS OF SCHIZOPHRENIA SPECTRUM DISORDERS IN THE SULFOTRANSFERASE 4A (SULT4A) GENE

(75) Inventors: Mark David Brennan, Jeffersonville, IN (US); Jodi Ann Condra, Louisville, KY (US); Amy Tabb Massey, Louisville, KY (US); Wei Wei, Galveston, TX (US); Holly Neibergs, Shelbyville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 229 days.

(21) Appl. No.: 11/323,061

(22) Filed: Dec. 30, 2005

(65) Prior Publication Data

US 2006/0177851 A1 Aug. 10, 2006

Related U.S. Application Data

(60) Provisional application No. 60/640,707, filed on Dec. 30, 2004.

(51) Int. Cl.
*C12Q 1/68* (2006.01)
*C12P 19/34* (2006.01)

(52) U.S. Cl. .............................. 435/6; 435/91.1; 436/63
(58) Field of Classification Search ........................ None
See application file for complete search history.

(56) References Cited

U.S. PATENT DOCUMENTS

| 5,474,796 | A | 12/1995 | Brennan et al. |
| 6,274,352 | B1 | 8/2001 | Schofield et al. |
| 2005/0209181 | A1 | 9/2005 | Akil et al. |

FOREIGN PATENT DOCUMENTS

| EP | 1 209 229 | 5/2002 |
| WO | WO 0078921 | 12/2000 |
| WO | WO 0180720 | 11/2001 |
| WO | WO03/102587 | 12/2003 |
| WO | WO 2004006838 | 1/2004 |

OTHER PUBLICATIONS

Riley et al., Eur. J. Human Genetics (2006), 14:669-680.*
Hegele et al. Arterioscler. Thromb. Vasc. Biol., 2002, vol. 22, pp. 1058-1061.*
Hattersley et al. Lancet, 2005, vol. 366, pp. 1315-1323.*
Ionnidis Plost Med, 2005, 2(8):e124.*
Kroese et al. Genetics in Medicine, vol. 6 (2004), p. 475-480.*
GeneCard, SULT4a1, pp. 1-13, available at www.genecard.com.*
Mummidi et al., J. Biol. Chem, 2000, vol. 275, pp. 18946-18961.*
Wall et al., Nature Genetics, 2003, vol. 4, p. 587-597.*
The dbSNP Build Process, SNP FAQ Archive, p. 1, available at www.ncbi.nlm.nih.gov.*
Brennan and Condra, "Transmission disequilibrium suggests a role for the sulfotransferase-4A1 gene in schizophrenia," Am. J. Med. Genet. Part B (Neuropsych. Genet.) 139B:69-72 (2005).

Bulayeva et al., "Mapping genes of complex psychiatric diseases in Daghestan genetic isolates," Am. J. Med. Genet. 6, 132B(1):76-84 (2004).
Chen et al., "Variants in the catechol-o-methyltransferase (COMT) gene are associated with schizophrenia in Irish high-density families," Mol. Psych. 9:962-7 (2004).
Clayton, "A generalization of the transmission/disequilibrium test for uncertain-haplotype transmission," Am. J. Hum. Genet. 65(4):1170-7 (1999).
Cloninger et al., "Genome-wide search for schizophrenia susceptibility loci: The NIMH genetics initiative and millennium consortium," Am. J. Med. Genet. 81:275-281 (1998).
Condra et al., "Evidence for two schizophrenia susceptibility genes on chromosome 22q13," Psych. Genet. 17(5):292-298 (2007).
Coon et al., "Genomic scan for genes predisposing to schizophrenia," Am. J. Med. Genet. 54(1):59-71 (1994).
DeLisi et al., "A genome-wide scan for linkage to chromosomal regions in 382 sibling pairs with schizophrenia or schizoaffective disorder," Am. J. Psych. 159:803-12 (2002).
Devaney et al., "No missense mutation of WKL1 in a subgroup of probands with schizophrenia," Mol. Psych. 7:419-423 (2002).
Ewald and Lundorf, "The missense mutation in the WKL1 gene not found in patients with bipolar affective disorder," Mol. Psych. 7:340-341 (2002).
Falany et al., "Molecular cloning and expression of novel sulphotransferase-like cDNAs from human and rat brain," Biochem. J. 346:857-64 (2000).
Fallin et al., "Bipolar I disorder and schizophrenia: A 440-single-nucleotide polymorphism screen of 64 candidate genes among Ashkenazi Jewish case-parent trios," Am. J. Hum. Genet. 77:918-936 (2005).
Fanous and Kendler, "The genetic relationship of personality to major depression and schizophrenia," Neurotox. Res. 6:43-50(2004).
Georgieva et al., "Genetic variation in the seven-pass transmembrane cadherin CELSR: Lack of association with schizophrenia," Psych. Genet. 13:103-6 (2003).
Gill et al., "A combined analysis of D22S278 marker alleles in affected sib-pairs: Support for a susceptibility locus for schizophrenia at chromosome 22q12," Schizophrenia Collaborative Linkage Group (Chromosome 22), Am. J. Med. Genet. 16:40-5 (1996).
Handoko et al., "Separate and interacting effects within the catechol-o-methyltransferase (COMT) are associated with schizophrenia," Mol. Psych. 10:589-597 (2005) [Epub ahead of print Oct. 26, 2004].
Ivanov et al., "Chromosome 22q11 deletions, velo-cardio-facial syndrome and early-onset psychosis," Molecular genetic study. Br. J. Psych. 183:409-13 (2003).
Jorgensen et al., "Search for common haplotypes on chromosome 22q in patients with schizophrenia or bipolar disorder from the Faroe Islands," Am. J. Med. Genet. (Neuropsych. Genet.) 114:245-252 (2002).
Kaganovich et al., "Is the WKL1 gene associated with schizophrenia?" Am. J. Med. Genet. 125B:31-7 (2004).
Kaufmann et al., "NIMH genetics initiative millennium schizophrenia consortium: Linkage analysis of African-American pedigrees," Am. J. Genet. 81:282-289 (1998).

(Continued)

*Primary Examiner*—Sarae Bausch
(74) *Attorney, Agent, or Firm*—Fish & Richardson P.C.

(57) ABSTRACT

The invention includes method of determining if a subject is at risk for developing schizophrenia (SZ), schizotypal personality disorder (SPD), or schizoaffective disorder (SD).

22 Claims, 1 Drawing Sheet

OTHER PUBLICATIONS

Kelsoe et al., "A genome survey indicates a possible susceptibility locus for bipolar disorder on chromosome 22," Proc. Natl. Acad. Sci. USA 98:585-90 (2001).

Lewis et al., "Genome scan meta-analysis of schizophrenia and bipolar disorder, part II: Schizophrenia," Am. J. Hum. Genet. 73:34-48 (2003).

Li et al., "Evidence for association between novel polymorphisms in the PRODH gene and schizophrenia in a Chinese population," Am. J. Med. Genet. 129B:13-5 (2004).

Liu et al., "Genetic variation at the 22q11 PRODH2/DGCR6 locus presents an unusual pattern and increases susceptibility to schizophrenia," Proc. Natl. Acad. Sci. USA 99:3717-22 (2002).

Liyou et al., "Localization of a brain sulfotransferase, SULT4A1, in the human and rat brain: An immunohistochemical study," J. Histochem. Cytochem. 51:1655-64 (2003).

Matise et al., "Systematic evaluation of map quality: Human chromosome 22," Am. J. Hum. Genet. 70:1398-410 (2002).

Maziade et al., "A search for specific and common susceptibility loci for schizophrenia and bipolar disorder: A linkage study in 13 target chromosomes," Mol. Psych. 6:684-93 (2001).

McGuffin et al., "Linkage and association studies of schizophrenia," Curr. Psych. Rep. 5:121-7 (2003).

McQuillin et al., "A novel polymorphism in exon 11 of the WKL1 gene, shows no association with schizophrenia," Eur. J. Hum. Gen. 10:491-494 (2002).

Meyer et al., "A missense mutation in a novel gene encoding a putative cation channel is associated with catatonic schizophrenia in a large pedigree," Mol. Psych. 6:302-6 (2001).

Meyer et al., "Association of WKL1/MLC1 with catatonic schizophrenia," Mol. Psych. 7:1037-38 (2002).

Mowry et al., "Multicenter linkage study of schizophrenia loci on chromosome 22q," Mol. Psych. 9(8):784-795 (2004).

Murphy, "Cognitive deficits associated with schizophrenia in velo-cardio-facial syndrome," Schizophr. Res. 70:223-32 (2004).

Myles-Worsley et al., "Linkage of a composite inhibitory phenotype to a chromosome 22q locus in eight Utah families," Am. J. Med. Genet. (Neuropsych. Genet.) 88:544-550 (1999).

Polymeropoulos et al., "Search for a schizophrenia susceptibility locus on human chromosome 22," Am. J. Med. Genet. 54:93-9 (1994).

Sakakibara et al., "Highly conserved mouse and human brain sulfotransferases: Molecular cloning, expression, and functional characterization," Gene 285:39-47 (2002).

Sanders et al., "Haplotypic association spanning the 22q11.21 genes COMT and ARVCF with schizophrenia," Mol. Psych. 10(4):353-65 (2004).

Severinsen et al., "Evidence implicating BRD1 with brain development and susceptibility to both schizophrenia and bipolar affective disorder," Mol. Psych. 11(12):1126-1138 (2006).

Shifman et al., "A highly significant association between a COMT haplotype and schizophrenia," Am. J. Hum. Genet. 71:1296-302 (2002).

Shirts and Nimgaonkar, "The genes for schizophrenia: Finally a breakthrough?" Curr. Psych. Rep. 6:303-12 (2004).

Stober et al., "Linkage and family-based association study of schizophrenia and the synapsin III locus that maps to chromosome 22q13," Am. J. Med. Genet. 96(3):392-397 (2000).

Stober et al., "Splitting schizophrenia: Periodic catatonia-susceptibility locus on chromosome 15q15," Am. J. Hum. Genet. 67:1201-1207 (2000).

Takahashi et al., "Genome-wide scan of homogeneous subtypes of NIMH genetics initiative schizophrenia families," Psych. Res. 133:111-122 (2005).

Takahashi et al., "Family-based association study of markers on chromosome 22 in schizophrenia using African-American, European-American, and Chinese families," Am. J. Med. Genet. 120B:11-17 (2003).

Vallada et al., "Chromosome 22 markers demonstrate transmission disequilibrium with schizophrenia," Psych. Genet. 5:127-30 (1995).

van Amelsvoort et al., "Cognitive deficits associated with schizophrenia in velo-cardio-facial syndrome," Schiz. Res. 70(2):223-232 (2004).

Williams and Owen, "Genetic abnormalities of chromosome 22 and the development of psychosis," Curr. Psych. Rep. 6(3):176-82 (2004).

Williams et al., "Detailed analysis of PRODH and PsPRODH reveals no association with schizophrenia," Am. J. Med. Genet. 120B:42-6 (2003).

"Hexanucleotide Mis of Boehringer Mannheim," *Boehringer Mannheim*, pp. 55-56 (1997).

Ioannidis, John, "Why most published research findings are false?" *PLoS Medicine*, 2(8):696-701 (2005).

Kroese et al., "Genetic tests and their evaluation: Can we answer the key questions?" *Genetics in Medicine*, 6(6):475-480 (2004).

Riley and Kendler, "Molecular genetic studies of schizophrenia," *European Journal of Human Genetics*, 14:669-680 (2006).

Carlson et al., "Mapping complex disease loci in whole-genome association studies," *Nature*, 429:446-452 (2004).

James et al., "BRCA1, a Potential Predictive Biomarker in the Treatment of Breast Cancer," *The Oncologist*, 12:142-150 (2007).

Meltzer et al., "Association of Sult4A1 SNPs with psychopathology and cognition in patients with schizophrenia or schizoaffective disorder," Manuscript—Vanderbilt University Medical Center, 2008.

Minchin et al., "Sulfotransferase 4A1," *Int. J. Biochem. Cell Biol.*, doi:10.1016/j.biocel.2007.11.010, (2008).

Morton et al., "The optimal measure of allelic association," *PNAS*, 98(9):5217-5221 (2001).

Severinsen et al., "Evidence implicating BRD1 with brain development and susceptibility to both schizophrenia and bipolar affective disorder," *Molecular Psychiatry*, 11:1126-1138 (2006).

Wang et al., "Evidence of common and specific genetic effects: association of the muscarinic acetylcholine receptor M2 (CHRM2) gene with alcohol dependence and major depressive syndrome," *Hum. Mol. Genet.*, 13:1903-1911 (2004).

Hong et al., "Association study of PICK1 rs3952 polymorphism and schizophrenia," Neuroreport, 15(12):1965-1967 (2004).

Saleem et al., "Association of CAG repeat loci on chromosome 22 with schizophrenia and bipolar disorder," Molecular Psychiatry, 6(6):694-700 (2001).

Verma et al., "A nonsense mutation in the Synaptogyrin 1 gene in a family with schizophrenia," Biological Psychiatry, 55(2):196-199 (2004).

\* cited by examiner

US 7,892,735 B2

GENETIC MARKERS OF SCHIZOPHRENIA SPECTRUM DISORDERS IN THE SULFOTRANSFERASE 4A (SULT4A) GENE

CLAIM OF PRIORITY

This application claims priority under 35 USC §119(e) to U.S. Provisional Patent Application Ser. No. 60/640,707, filed on Dec. 30, 2004, the entire contents of which are hereby incorporated by reference.

STATE SPONSORED RESEARCH OR DEVELOPMENT

This invention was made in part with an award from the Kentucky Science and Technology Corporation under Contract No. 144-401-06.

TECHNICAL FIELD

This invention relates to genetic markers of schizophrenia, and methods of use thereof.

BACKGROUND

Numerous linkage and association studies have implicated chromosome 22q in the etiology of schizophrenia (Vallada et al., Psychiatr. Genet. 5:127-30 (1995); Gill et al., Am. J. Med. Genet. 16:40-5 (1996); Myles-Worsley et al., Am. J. Med. Genet. 88:544-50 (1999); Jorgensen et al., Am. J. Med. Genet. 114:245-52 (2002); DeLisi et al., Am. J. Psychiatry 159:803-12 (2002); Lewis et al., Am. J. Hum. Genet. 73:34-48 (2003); Takahashi et al., Am. J. Med. Genet. 120B:11-7 (2003)). Nonetheless, the precise location of the genes involved has yet to be resolved.

Possibly owing to genetic heterogeneity, analyses of positional candidates on this chromosome have resulted in conflicting results. The 22q11 region has received much attention, as its deletion in velo-cardio-facial syndrome correlates with increased propensity to develop schizophrenia (Ivanov et al., Br J Psychiatry. 183:409-13 (2003); van Amelsvoort et al., Genetic Curr. Psychiatry. Rep. 6:176-82 (2004); Williams and Owen, Curr Psychiatry Rep. 6(3): 176-82 (2004)). Candidates identified in this region include the catechol-O-methyltransferase (COMT) gene, an attractive candidate whose role has recently been challenged, and proline dehydrogenase, a gene whose role may be limited to Chinese lineages (Shifman et al., Am. J. Hum. Genet. 71:1296-302 (2002); Williams and Owen, (2004), supra; McGuffin et al., Curr. Psychiatry. Rep. 5:121-7 (2003); Williams et al., Am. J. Med. Genet. 120B:42-6 (2003); Handoko et al., Mol Psychiatry. 10:589-597 (2005) [Epub ahead of print Oct. 26, 2004]; Shirts and Nimgaonkar, Curr. Psychiatry. Rep. 6:303-12 (2004)). Other studies suggest a more distal location for a susceptibility gene in 22q12 or 22q13 (DeLisi et al., 2002, supra; Takahashi et al., Am. J. Med. Genet. 120B:11-7 (2003) et al., 2003). Here again, however, family-based transmission studies and evaluation of specific candidate genes have provided somewhat modest or, at times, contradictory, results (Vallada et al., Psychiatr. Genet. 5:127-30 (1995); Stober et al., Am. J. Med. Genet. 96:392-7 (2000); Meyer et al., Mol. Psychiatry 6:302-6 (2001); Takahashi et al., Am. J. Med. Genet. 120B:11-7 (2003); Georgieva et al., Psychiatr. Genet. 13:103-6 (2003); Kaganovich et al., Am. J. Med. Genet. 125B:31-7 (2004)).

Due to the severity of the disorder, the negative impact of a psychotic episode on a patient, and the diminishing recovery after each psychotic episode, there is a need to more conclusively identify individuals who have or are at risk of developing schizophrenia (SZ), schizotypal personality disorder (SPD) or schizoaffective disorder (SD), for example, to confirm clinical diagnoses, to allow for prophylactic therapies, to determine appropriate therapies based on their genotypic subtype, and to provide genetic counseling for prospective parents with a history of the disorder.

SUMMARY

In previous work the present inventors developed a high quality linkage genetic map of chromosome 22 that included two extreme distal markers (Brennan et al., Genomics 63:430-432 (2000); Matise et al., Am. J. Hum. Genet. 70:1398-410 (2002)). These and other highly informative microsatellite markers (including a new microsatellite marker targeting the promoter region of the Sult4a1 gene) were used to evaluated 27 families from the NIMH Schizophrenia Genetics Initiative. Based on the linkage and family-based association patterns that were observed, a multi-locus model involving at least the Sult4A1 region and a more distal region near marker D22s256 in 22q13 is described herein. Thus, the invention includes methods of determining risk of developing schizophrenia (SZ), schizotypal personality disorder (SPD) or schizoaffective disorder (SD) as described herein.

In one aspect, the invention includes methods for obtaining information regarding a subject's risk for developing SZ, SD or SPD. The methods include obtaining a test haplotype associated with schizophrenia as described herein. The methods can also include obtaining a sample comprising genomic DNA (gDNA) from the subject, and determining the identity, absence or presence of a test haplotype associated with SZ, SD or SPD as described herein. In some embodiments, the methods include obtaining a test haplotype for the subject comprising at least one test marker that is within 1 linkage disequilibrium unit (1 LDU) of a marker listed in Table 4, 6, 7, 8 or 9, wherein the haplotype provides information regarding the subject's risk of developing SZ, SPD, or SD. In some embodiments, the test marker is a marker listed in one or more of tables 4, 6, 7, 8, or 9, or a marker within 1 linkage disequilibrium unit (1 LDU) or >0.5 D' of a polymorphism described herein, e.g., markers in a region of chromosome 22, e.g., in 22q13, e.g., in 22q13.3, that is between and including SNPs rs738596, rs738598, or rs135221 on the proximal end, and rs13884 or rs137853 on the distal end, e.g., between rs738596 and rs137853.

In some embodiments, the test marker is within 1 LDU of a marker listed in Table 6, 7, 8, or 9, and is in a region of 22q13 that is between and including SNPs rs738596, rs738598, or rs135221 on the proximal end, and rs137853 or rs13884 on the distal end.

In some embodiments, the test haplotype includes at least one marker listed in Table 4, 6, 7, 8 or 9.

In some embodiments, the test haplotype includes one or more of: microsatellite marker D22S526, and/or a polymorphism of Sulfotransferase 4A1 (Sult4a1), e.g., rs138060, rs138097, rs138110, and/or D22s1749e. In some embodiments, the polymorphism is an allele of Sult4a1 at microsatellite marker D22s1749e comprising more than 207 nucleotides, and indicates that the subject has an increased risk of developing SZ, SPD, or SD.

In some embodiments, the test haplotype includes at least two markers, one of which is microsatellite marker D22S526.

In some embodiments, the test haplotype includes at least one marker listed in Table 4 or 9, or in bold in table 8, and provides information regarding a subject's risk of developing SZ, under a narrower (DSM III) disease definition.

The methods described herein can include obtaining a haplotype that includes two or more, e.g., two, three, four, five, or six markers.

Additionally, the methods can include determining the presence or absence of other markers known to be associated with SZ, SD or SPD, e.g., outside of a region identified herein. A number of other such markers are known in the art, e.g., as described herein.

The subject can be a mammal, e.g., a primate, preferably a higher primate, e.g., a human (e.g., a patient having, or at risk of, SZ, SD or SPD). In one embodiment, the subject is a patient having SZ, SD or SPD (e.g., a patient suffering from early, intermediate or aggressive SZ, SD or SPD). In some embodiments, the methods described herein are used to obtain information regarding a subject's risk of developing SZ, SD or SPD, wherein the disorder is other than catatonic schizophrenia. In some embodiments, the subject is of African American (AA) or European American (EA) descent, i.e., has one or more ancestors who are AA or EA.

In one embodiment, a subject to be evaluated by a method described herein is a subject having one or more risk factors associated with SZ, SPD or SD. For example, the subject may have a relative afflicted with SZ, e.g., one or more of a grandparent, parent, uncle or aunt, sibling, or child who has or had SZ, SPD or SD; the subject may have a genetically based phenotypic trait associated with risk for SZ, SPD or SD (e.g., eye tracking dysfunction); deficits in working (short-term) memory; and/or mixed-handedness (the use of different hands for different tasks), particularly in females.

In some embodiments, the subject is a child, fetus, or embryo, and one of the subject's relatives, e.g., a parent or sibling, of the child, fetus, or embryo has SZ, SPD or SD. In this case, the presence in the child, fetus, or embryo of a haplotype described herein that is shared with the affected parent, but not with the non-affected parent, indicates that the child, fetus, or embryo has an increased risk of developing SPD, SD, or SZ. In some embodiments, the subject has no overt or clinical signs of SZ, SPD, or SD.

In some embodiments, obtaining a test haplotype includes obtaining a sample comprising DNA from the subject; and determining the identity, presence or absence of at least one test marker that is within 1 LDU of a marker listed in Table 4, 6, 7, 8 or 9 in the DNA. The sample can be obtained, e.g., from the subject by a health care provider, or provided by the subject without the assistance of a health care provider.

In some embodiments, obtaining a test haplotype includes reviewing a subject's medical history, wherein the medical history includes information regarding the presence or absence of at least one test marker that is within 1 LDU of a marker listed in Table 4, 6, 7, 8 or 9 in the subject.

In some embodiments, the methods described herein include obtaining a reference haplotype including a reference marker that corresponds to a test marker, and comparing the test haplotype to the reference haplotype. A reference marker that "corresponds to" a test marker is the same marker. For example, if the test haplotype includes D22S526, then the reference haplotype should also include D22S526 for comparison purposes. The sharing of a haplotype (e.g., of some or all of the markers) between the test haplotype and a reference haplotype is indicative of whether there is an increased likelihood that the subject will develop SZ, SPD, or SD.

In some embodiments, the methods include administering a treatment to a subject identified as being at increased risk for developing SZ, SPD, or SD, e.g., a pharmacological or psychosocial treatment as described herein. In some embodiments, the subject has no overt or clinical signs of SZ, SPD, or SD, and the treatment is administrated before any such signs appear.

Information obtained using a method described herein can be used, e.g., to select a subject population for a clinical trial, to stratify a subject population in a clinical trial, and/or to stratify subjects that respond to a treatment from those who do not respond to a treatment, or subjects that have negative side effects from those who do not.

In another aspect, the invention provides methods for selecting a subject for inclusion in a clinical trial, e.g., a trial of a treatment for SZ, SPD, or SD. The methods include obtaining a haplotype for the subject including at least one marker that is within 1 linkage disequilibrium unit (1 LDU) of a marker listed in Tables 4, 6, 7, 8 or 9; determining whether the haplotype is associated with an increased risk of developing schizophrenia (SZ), schizotypal personality disorder (SPD), or schizoaffective disorder (SD); and including the subject in the trial if the haplotype indicates that the subject has an increased risk of developing SZ, SPD, or SD.

In another aspect, the invention provides methods for selecting a subject for administration of a treatment for schizophrenia (SZ), schizotypal personality disorder (SPD), or schizoaffective disorder (SD). The methods include obtaining a haplotype for the subject, wherein the haplotype comprises at least one marker that is within 1 linkage disequilibrium unit (1 LDU) of a marker listed in Tables 4, 6, 7, 8 or 9; determining whether the haplotype is associated with an increased risk of developing SZ, SPD, or SD; and administering the treatment to the subject if the haplotype indicates that the subject has an increased risk of developing SZ, SPD, or SD.

In another aspect, the invention provides methods for selecting a treatment for administration to a subject. The methods include obtaining a haplotype for the subject, wherein the haplotype comprises at least one marker that is within 1 linkage disequilibrium unit (1 LDU) of a marker listed in Tables 4, 6, 7, 8 or 9; determining whether the haplotype is associated with an increased risk of developing schizophrenia (SZ), schizotypal personality disorder (SPD), or schizoaffective disorder (SD); and administering the treatment for SZ, SPD, or SD to the subject if the haplotype indicates that the subject has an increased risk of developing SZ, SPD, or SD.

In another aspect, the invention provides methods for evaluating the effect of a haplotype on the outcome of a treatment for schizophrenia (SZ), schizotypal personality disorder (SPD), or schizoaffective disorder (SD). The methods include obtaining information regarding outcome of the treatment, wherein the information comprises a parameter relating to the treatment of each subject in a population of subjects; obtaining haplotypes for each subject in the population, wherein the haplotype comprises at least one marker that is within 1 linkage disequilibrium unit (1 LDU) of a marker listed in Tables 4, 6, 7, 8 or 9; and correlating the information regarding outcome with the haplotypes; thereby evaluating the effect of the haplotype on the outcome of the treatment.

In some embodiments, the method includes selecting a treatment for administration to a subject who has a selected haplotype, based on the effect of the haplotype on the outcome of the treatment.

In some embodiments, the information regarding outcome of the treatment is from a completed clinical trial, and the analysis is retrospective.

In another aspect, the invention features methods of predicting a subject's risk of developing SZ, SPD, or SD. The methods include obtaining a reference haplotype. In some embodiments, the reference haplotype is from at least one of the following relatives of the subject: (i) a parent who has SZ, SPD, or SD; (ii) a sibling who has SZ, SPD, or SD, and an unaffected parent; or (iii) a second degree relative (e.g., aunt, uncle, or grandparent) who has SZ, SPD, or SD, and an unaffected parent; obtaining a test haplotype from the subject in the same region; and comparing the test haplotype to a reference haplotype. The sharing of a haplotype in this region between the test haplotype and a reference haplotype from a relative having the disorder is an indication of an increased likelihood that the subject will develop SZ, SPD, or SD. In some embodiments, the reference haplotype is from an unaffected individual, and sharing of a haplotype indicates that there is no increased likelihood that the subject will develop SZ, SD, or SD.

In a further aspect, the invention features methods for detecting the presence of a haplotype associated with susceptibility to SZ, SPD, or SD in a subject, by analyzing a sample of DNA from the subject.

Additionally, the invention features methods of predicting a test subject's risk of developing SZ, SPD, or SD. The methods include obtaining a reference haplotype of a reference subject, wherein the reference subject has SZ, SPD, or SD; determining a test haplotype of the test subject in the same region; and comparing the test haplotype to the reference haplotype, wherein the sharing of a haplotype in this region between the test subject and the reference subject is an indication of an increased likelihood that the test subject will develop SZ, SPD, or SD. In some embodiments, the method further includes comparing the subject's haplotype to a reference subject who does not have SZ, SPD, or SD.

Further, the invention features methods for predicting a test subject's risk of developing SZ. The methods include obtaining a reference haplotype of a reference subject in a region described herein, wherein the reference subject has SZ; obtaining a test haplotype of the test subject in the same region; and comparing the test haplotype to the reference haplotype. The sharing of a haplotype in this region between the test subject and the reference subject is an indication of an increased likelihood that the test subject will develop SZ. In some embodiments, the method also includes comparing the test subject's haplotype to a reference subject who does not have SZ.

In another aspect, the invention features methods for predicting a subject's risk of developing SZ, SPD, or SD. The methods include obtaining genomic DNA (gDNA) from the subject; and determining the absence or presence of a haplotype associated with SZ at human chromosome 22q13 as described herein. The presence of a haplotype associated with SZ, SPD, or SD indicates that the subject has an increased risk of developing SZ, SD or SPD.

The invention further features nucleic acid probes having a nucleotide sequence that hybridizes with a nucleotide sequence within human chromosome 22q13 and allows detection of a microsatellite marker at D22s1749E, e.g., under hybridization conditions of a 50% formamide, 2×SSC wash for 10 minutes at 45° C. followed by a 2×SSC wash for 10 minutes at 37° C. In some embodiments, the probes are at least 20 nucleotides long and include all or part of 5'-CAGC-CGCACGCCATGGAACTCGAAG-3' (SEQ ID NO:1) or 5'-GGCGCCATGACGTCACGCCTGC-3' (SEQ ID NO:2). In some embodiments, the probes are no longer than 30, 50, 100, 200, or 500 nucleotides long.

Also provided herein are kits for use in detection of haplotypes associated with SZ, SD or SPD, including at least one nucleic acid probe that hybridizes to a sequence that includes a polymorphism described herein, or can be used to amplify a sequence that includes a polymorphism described herein.

Also provided are arrays that include a substrate having a plurality of addressable areas, wherein one or more of the addressable areas includes one or more probes that can be used to detect a polymorphism described herein.

In another aspect, the invention provides methods for providing information regarding a subject's risk of developing schizophrenia (SZ), schizotypal personality disorder (SPD), or schizoaffective disorder (SD). The methods include obtaining a sample from the subject at a first site; transferring the sample to a second site for analysis, wherein the analysis provides data regarding the identity, presence or absence of at least one test marker that is within 1 LDU of a marker listed in Tables 4, 6, 7, 8 or 9; and transferring the data to one or more of a health care provider, the subject, or a healthcare payer. In some embodiments, the first site is a health care provider's place of business, or is not a health care provider's place of business, e.g., the subject's home.

In some embodiments, the data is transferred to a healthcare payer and used to decide whether to reimburse a health care provider.

DEFINITIONS

As used herein, a "haplotype" is a set of signature genetic changes (polymorphisms) that are normally grouped closely together on the DNA strand, and are usually inherited as a group; the polymorphisms are also referred to herein as "markers." A "haplotype" as used herein is information regarding the presence or absence of one or more genetic markers in a subject. A haplotype can consist of a variety of genetic markers, including indels (insertions or deletions of the DNA at particular locations on the chromosome); single nucleotide polymorphisms (SNPs) in which a particular nucleotide is changed; microsatellites; and minisatellites.

Microsatellites (sometimes referred to as a variable number of tandem repeats or VNTRs) are short segments of DNA that have a repeated sequence, usually about 2 to 5 nucleotides long (e.g., CACACA), that tend to occur in non-coding DNA. Changes in the microsatellites sometimes occur during the genetic recombination of sexual reproduction, increasing or decreasing the number of repeats found at an allele, changing the length of the allele. Microsatellite markers are stable, polymorphic, easily analyzed and occur regularly throughout the genome, making them especially suitable for genetic analysis.

"Linkage disequilibrium" refers to when the observed frequencies of haplotypes in a population does not agree with haplotype frequencies predicted by multiplying together the frequency of individual genetic markers in each haplotype.

The term "chromosome" as used herein refers to a gene carrier of a cell that is derived from chromatin and comprises DNA and protein components (e.g., histones). The conventional internationally recognized individual human genome chromosome numbering identification system is employed herein. The size of an individual chromosome can vary from one type to another with a given multi-chromosomal genome and from one genome to another. In the case of the human genome, the entire DNA mass of a given chromosome is usually greater than about 100,000,000 base pairs. For example, the size of the entire human genome is about $3 \times 10^9$ base pairs. Chromosome 22 contains about $5.3 \times 10^7$ base pairs (see, e.g., Yunis, Science 191:1268-1270 (1976), and Kavenoff et al., Cold Spring Harbor Symposia on Quantitative Biology 38:1-8 (1973)).

The term "gene" refers to a DNA sequence in a chromosome that codes for a product (either RNA or its translation product, a polypeptide). A gene contains a coding region and includes regions preceding and following the coding region (termed respectively "leader" and "trailer"). The coding region is comprised of a plurality of coding segments ("exons") and intervening sequences ("introns") between individual coding segments.

The term "probe" refers to an oligonucleotide. A probe can be single stranded at the time of hybridization to a target. As used herein, probes include primers, i.e., oligonucleotides that can be used to prime a reaction, e.g., a PCR reaction.

The term "label" or "label containing moiety" refers in a moiety capable of detection, such as a radioactive isotope or group containing same, and nonisotopic labels, such as enzymes, biotin, avidin, streptavidin, digoxygenin, luminescent agents, dyes, haptens, and the like. Luminescent agents, depending upon the source of exciting energy, can be classified as radioluminescent, chemiluminescent, bioluminescent, and photoluminescent (including fluorescent and phosphorescent). A probe described herein can be bound, e.g., chemically bound to label-containing moieties or can be suitable to be so bound. The probe can be directly or indirectly labeled.

The term "direct label probe" (or "directly labeled probe") refers to a nucleic acid probe whose label after hybrid formation with a target is detectable without further reactive processing of hybrid. The term "indirect label probe" (or "indirectly labeled probe") refers to a nucleic acid probe whose label after hybrid formation with a target is further reacted in subsequent processing with one or more reagents to associate therewith one or more moieties that finally result in a detectable entity.

The terms "target," "DNA target," or "DNA target region" refers to a nucleotide sequence that occurs at a specific chromosomal location. Each such sequence or portion is preferably at least partially, single stranded (e.g., denatured) at the time of hybridization. When the target nucleotide sequences are located only in a single region or fraction of a given chromosome, the term "target region" is sometimes used. Targets for hybridization can be derived from specimens which include, but are not limited to, chromosomes or regions of chromosomes in normal, diseased or malignant human cells, either interphase or at any state of meiosis or mitosis, and either extracted or derived from living or postmortem tissues, organs or fluids; germinal cells including sperm and egg cells, or cells from zygotes, fetuses, or embryos, or chorionic or amniotic cells, or cells from any other germinating body; cells grown in vitro, from either long-term or short-term culture, and either normal, immortalized or transformed; inter- or intraspecific hybrids of different types of cells or differentiation states of these cells; individual chromosomes or portions of chromosomes, or translocated, deleted or other damaged chromosomes, isolated by any of a number of means known to those with skill in the art, including libraries of such chromosomes cloned and propagated in prokaryotic or other cloning vectors, or amplified in vitro by means well known to those with skill; or any forensic material, including but not limited to blood, or other samples.

The term "hybrid" refers to the product of a hybridization procedure between a probe and a target.

The term "hybridizing conditions" has general reference to the combinations of conditions that are employable in a given hybridization procedure to produce hybrids, such conditions typically involving controlled temperature, liquid phase, and contact between a probe (or probe composition) and a target. Conveniently and preferably, at least one denaturation step precedes a step wherein a probe or probe composition is contacted with a target. Guidance for performing hybridization reactions can be found in Ausubel et al., *Current Protocols in Molecular Biology*, John Wiley & Sons, N.Y. (2003), 6.3.1-6.3.6. Aqueous and nonaqueous methods are described in that reference and either can be used. Hybridization conditions referred to herein are a 50% formamide, 2×SSC wash for 10 minutes at 45° C. followed by a 2×SSC wash for 10 minutes at 37° C.

Calculations of "identity" between two sequences can be performed as follows. The sequences are aligned for optimal comparison purposes (e.g., gaps can be introduced in one or both of a first and a second nucleic acid sequence for optimal alignment and non-identical sequences can be disregarded for comparison purposes). The length of a sequence aligned for comparison purposes is at least 30%, e.g., at least 40%, 50%, 60%, 70%, 80%, 90% or 100%, of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In some embodiments, the percent identity between two nucleotide sequences is determined using the GAP program in the GCG software package, using a Blossum 62 scoring matrix with a gap penalty of 12, a gap extend penalty of 4, and a frameshift gap penalty of 5.

As used herein, the term "substantially identical" is used to refer to a first nucleotide sequence that contains a sufficient number of identical nucleotides to a second nucleotide sequence such that the first and second nucleotide sequences have similar activities. Nucleotide sequences that are substantially identical are at least 80%, e.g., 85%, 90%, 95%, 97% or more, identical.

The term "nonspecific binding DNA" refers to DNA which is complementary to DNA segments of a probe, which DNA occurs in at least one other position in a genome, outside of a selected chromosomal target region within that genome. An example of nonspecific binding DNA comprises a class of DNA repeated segments whose members commonly occur in more than one chromosome or chromosome region. Such common repetitive segments tend to hybridize to a greater extent than other DNA segments that are present in probe composition.

As used herein, the term "stratification" refers to the creation of a distinction between subjects on the basis of a characteristic or characteristics of the subjects. Generally, in the context of clinical trials, the distinction is used to distinguish responses or effects in different sets of patients distinguished according to the stratification parameters. In some embodiments, stratification includes distinction of subject groups based on the presence or absence of particular markers or haplotypes described herein. The stratification can be performed, e.g., in the course of analysis, or can be used in creation of distinct groups or in other ways.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting.

All publications, patent applications, patents, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

Like reference symbols in the various drawings indicate like elements.

DETAILED DESCRIPTION

Figure 1:
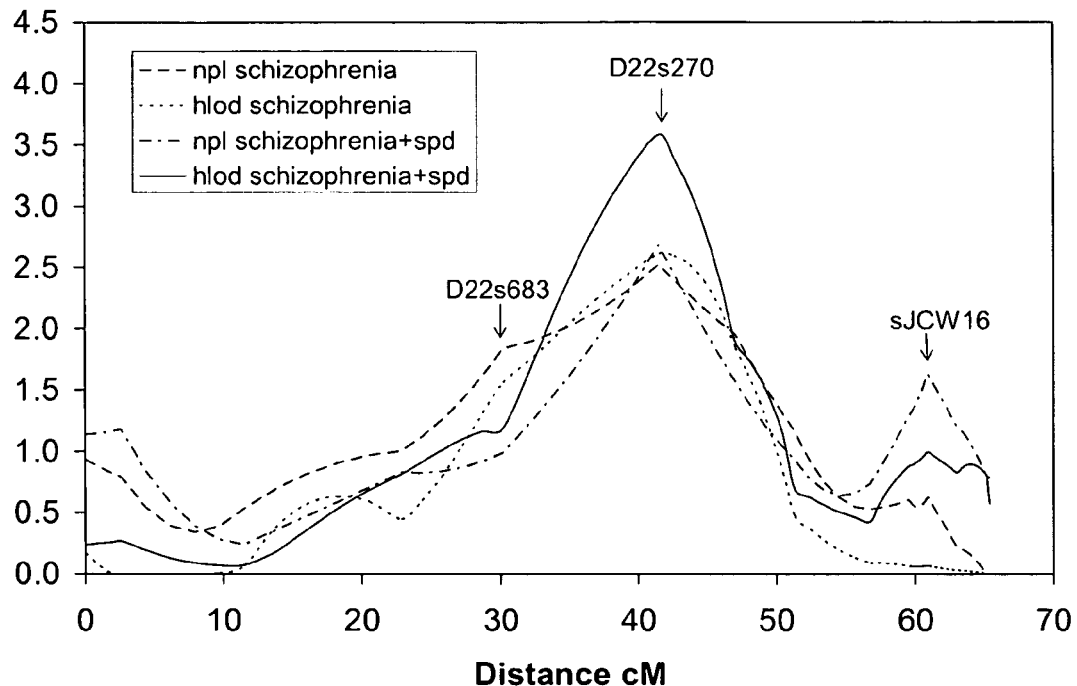
FIG. 1 is a line graph illustrating LOD scores for markers at the indicated locations on the long arm of chromosome 22. The locations of markers D22s683, D22s270, and sJCW16, which are associated with the highest LOD scores, are shown.

The methods described herein are based, at least in part, on the discovery of haplotypes and markers in 22q13 that are associated with increased risk of developing schizophrenia (SZ), schizotypal personality disorder (SPD) or schizoaffective disorder (SD). As described herein, TDT analysis provided suggestive evidence of role of Sult4a1 in this set of families (P=0.002 for narrowly-defined SZ, 0.04 for SZ+SPD), with a tendency for one of the longer alleles of D22S1749E to be preferentially transferred to affected children (See Examples, below). Additionally, TDT analysis for the other microsatellite markers suggests that a region near marker D22S526 plays a role in SZ (P=0.003, for narrowly-defined SZ; P=0.00009 for SZ+SD+SPD). Thus, segments of chromosome 22 near Sult4a1 and D22S526 contain sequences that are linked to a predisposition to SPD, SD and SZ.

Methods of Diagnoses and Evaluation of Risk

Described herein are a variety of methods for the diagnosis of susceptibility to SZ, SPD or SD. "Susceptibility" does not necessarily mean that the subject will develop SZ, SPD or SD, but rather that the subject is, in a statistical sense, more likely to develop SZ than an average member of the population, i.e., has an increased risk of developing SZ, SPD, or SD. As used herein, susceptibility to SZ exists if the subject has a haplotype associated with an increased risk of SZ, SPD, or SD as described herein. Ascertaining whether the subject has such a haplotype is included in the concept of diagnosing susceptibility to SZ, SPD or SD as used herein. Such determination is useful, for example, for purposes of diagnosis, treatment selection, and genetic counseling. Thus, the methods described herein can include obtaining a haplotype associated with an increased risk of SZ, SPD, or SD as described herein for the subject.

As used herein, "obtaining a haplotype" includes obtaining information regarding the identity, presence or absence of one or more genetic markers in a subject. Obtaining a haplotype can, but need not, include obtaining a sample comprising DNA from a subject, and/or assessing the identity, presence or absence of one or more genetic markers in the sample. The individual or organization who obtains the haplotype need not actually carry out the physical analysis of a sample from a subject; the haplotype can include information obtained by analysis of the sample by a third party. Thus the methods can include steps that occur at more than one site. For example, a sample can be obtained from a subject at a first site, such as at a health care provider, or at the subject's home in the case of a self-testing kit. The sample can be analyzed at the same or a second site, e.g., at a laboratory or other testing facility.

Obtaining a haplotype can also include or consist of reviewing a subject's medical history, where the medical history includes information regarding the identity, presence or absence of one or more genetic markers in the subject, e.g., results of a genetic test.

In some embodiments, to detect the presence of a haplotype described herein, a biological sample that includes nucleated cells (such as blood, a cheek swab or mouthwash) is prepared and analyzed for the presence or absence of preselected markers. Such diagnoses may be performed by diagnostic laboratories, or, alternatively, diagnostic kits can be manufactured and sold to health care providers or to private individuals for self-diagnosis. Diagnostic or prognostic tests can be performed as described herein or using well known techniques, such as described in U.S. Pat. No. 5,800,998.

Results of these tests, and optionally interpretive information, can be returned to the subject, the health care provider or to a third party payor. The results can be used in a number of ways. The information can be, e.g., communicated to the tested subject, e.g., with a prognosis and optionally interpretive materials that help the subject understand the test results and prognosis. The information can be used, e.g., by a health care provider, to determine whether to administer a specific drug, or whether a subject should be assigned to a specific category, e.g., a category associated with a specific disease endophenotype, or with drug response or non-response. The information can be used, e.g., by a third party payor such as a healthcare payer (e.g., insurance company or HMO) or other agency, to determine whether or not to reimburse a health care provider for services to the subject, or whether to approve the provision of services to the subject. For example, the healthcare payer may decide to reimburse a health care provider for treatments for SZ, SPD or SD if the subject has an increased risk of developing SZ, SPD or SD. As another example, a drug or treatment may be indicated for individuals with a certain haplotype, and the insurance company would only reimburse the health care provider (or the insured individual) for prescription or purchase of the drug if the insured individual has that haplotype. The presence or absence of the haplotype in a patient may be ascertained by using any of the methods described herein.

Information gleaned from the methods described herein can also be used to select or stratify subjects for a clinical trial. For example, the presence of a selected haplotype described herein can be used to select a subject for a trial. The information can optionally be correlated with clinical information about the subject, e.g., diagnostic or endophenotypic information.

Haplotypes Associated with SZ, SPD and SD

As described herein, haplotypes associated with SZ, SPD or SD include markers 10 in the distal region of the long arm of chromosome 22 (i.e., in 22q13.3) as exemplified by the transmission disequilibrium results shown in tables 4, 6, 7, 8 or 9.

As one example, haplotypes associated with a broader disorder definition including SZ, SPD and SD include one or more markers on chromosome 22 that are within 1 linkage disequilibrium unit (1 LDU) of a marker listed in Tables 4, 6, 7, 8 or 9. In some embodiments, the haplotype includes one or more of the markers listed in tables 4, 6, 7, 8 or 9. In some embodiments, the markers are in a region of 22q13 that is between and includes SNPs rs738596, rs738598, or rs135221 on the proximal end, and rs13884 or rs137853 on the distal end. In some embodiments, the markers are in a region of 22q13 that is between and includes SNPs rs738598 and rs13884. In some embodiments, the markers are in a region of 22q13 that is between and includes SNPs rs135221 and rs13884.

Haplotypes associated with a narrower disorder definition of SZ can include one or more markers that are within 1 LDU of a marker listed in Table 4 or 9, or in bold in table 8. In some embodiments, the haplotype includes one or more of the markers listed in Tables 4 or 9, or in bold in table 8. In some embodiments, the markers are in a region of 22q13 that is between and includes rs135221 on the proximal end, and rs13884 on the distal end.

In some embodiments, the methods include determining the presence of a haplotype that includes one or more polymorphisms near D22S526 and/or the polymorphisms in the Sult4a1 gene listed in Table 4, and/or polymorphisms within 1 LDU of these markers.

In some embodiments, the methods described herein do not include detecting polymorphisms within the MLC1 gene.

Sulfotransferase-4A1 (Sult4a1)

Using samples obtained from the National Institutes of Mental Health Schizophrenia Genetics Initiative, 27 nuclear families having multiple siblings with schizophrenia and schizophrenia-spectrum disorders were evaluated for linkage to chromosome 22 markers. Analysis with 14 highly informative microsatellite markers provided evidence for linkage near marker D22s270. Assuming heterogeneity, a maximum LOD score of 2.90 was obtained using DSM IV criteria, and a maximum LOD score of 3.96 was obtained for a broader disease definition that included schizotypal personality disorder (SPD). Nonparametric linkage analysis provided suggestive evidence for linkage at the same location (LOD scores of 2.6 and 2.8 for the narrow and broad definitions, respectively).

This segment of chromosome 22 contains the sulfotransferase-4A1 (Sult4a1) gene, which encodes a brain-specific sulfotransferase believed to be involved in metabolism of neurotransmitters (Falany et al., Biochem J. 346:857-64 (2000); Sakakibara et al., Gene 285:39-47 (2002); Liyou et al., J. Histochem. Cytochem. 51:655-64 (2003)). This positional candidate was evaluated by family-based TDT analysis of 27 families from the NIMH Schizophrenia Genetics Initiative. To evaluate this candidate gene, a microsatellite marker (D22S 1749E) targeting a promoter polymorphism in the gene was developed, and transmission disequilibrium (TDT) analysis of this marker and three single nucleotide polymorphisms spanning a 37 kb region containing the gene was performed.

As described herein, TDT analysis provided suggestive evidence of role of Sult4a1 in this set of families (P=0.002 for narrowly-defined SZ, 0.04 for SZ+SPD), with a tendency for one of the longer alleles (213 nt) of D22S1749E to be preferentially transferred to affected children (See Examples 1-4, below).

The sample was expanded by the addition of 17 further families to the original 27 families. Using the D22S1749E marker in linkage analysis for the pooled sample (using a dominant model assuming genetic heterogeneity, a penetrance of 50% for a heterozyote and a 1% allele frequency) a single point heterogeneous LOD score of 4.78 was obtained for the combined sample of 44 families ($\alpha$=0.7). Consistent with the initial findings, for the pooled sample, D22S1749E shows significant deviation from expectation for transmission to affected offspring using TRANSMIT (P=0.015 for SZ, and P=0.006 for the broader definition including SPD).

Thus, the methods described herein can include detecting the identity, presence or absence of one or more polymorphisms of the Sult4a1 gene, e.g., polymorphisms described herein. For example, the methods described herein can include determining the presence of a polymorphism at D22S1749E, e.g., determining the length of the alleles at D22S1749E. In some embodiments the methods also include detecting the presence of a SNP in the Sult4a1 gene, e.g., one or more of rs138060, rs138097, and rs138110 (see, e.g., Example 3 and Table 4).

D22S526 and the Distal Region of 22q13

Numerous two and three SNP haplotypes spanning the distal region of 22q13 show highly significant distortions in transmission ratios for DSM-IIIR diagnosed SZ and broader disease definitions (see the Examples, below; $P<10^{-5}$). Some of these remain significant even after the most parsimonious corrections for multiple comparisons (Risch and Merikangas, Science 273(5281):1516-7 (1996); Sabatti et al., Genetics 164(2):829-33 (2003)). One SNP by itself, rs1573726, shows significant TDT values by this method ($X^2$=15.6, 1 df, P=7.8×$10^{-5}$).

Thus, the methods described herein include identifying subjects on the basis of having a haplotype that includes polymorphisms that are in the region of chromosome 22 that is defined by the SNPs rs738596 (on the proximal end) and rs137853 (on the distal end). In some embodiments, the methods include identifying haplotypes that include polymorphisms between SNPs rs738598 (proximal) and rs137853 or rs138844 (distal), or between rs135221 (proximal) and rs137853 or rs138844 (distal). Proximal refers to a location that is nearer the centromere, distal is further away. In some embodiments, the methods do not include the evaluation of polymorphisms at microsatellite D22s1169.

A close evaluation of the haplotypes revealed an interesting pattern. Indeed, there are particular SNP haplotypes preferentially transmitted, and these differ somewhat in EA (European American) and AA (African American) families. Some are not rare, but fairly common haplotypes having 25 to 40% expected frequencies based on information now available through the haplotyping consortium (on the world wide web at hapmap.org). However, in about half of the NIMH families, these SNP haplotypes occur as part of a larger haplotype involving a small subset (two to four per population) of the 23 alleles of the highly polymorphic marker D22s526. TDT analysis for the other microsatellite markers suggests that a region near marker D22S526 plays a role in SZ (P=0.003, for narrowly-defined SZ; P=0.00009 for SZ+SPD+SD), possibly due to microdeletions of the region immediately surrounding and including this highly polymorphic marker (see Examples 4 and 7, below). Thus, in some embodiments, the methods described herein include the evaluation of polymorphisms of D22S526, to detect microdeletions e.g., microdeletions that include D22S526, e.g., microdeletions of at least 50, 100, 200, 300, 400, 500 or more Kb. In some embodiments, the microdeletions appear as apparent homozygosity, and the presence of homozygosity at D22S526 is indicative of an increased risk of developing SZ, SD, or SPD.

Linkage Disequilibrium Analysis

Linkage disequilibrium (LD) is a measure of the degree of association between alleles in a population. One of skill in the art will appreciate that haplotypes involving markers within 1 Linkage Disequilibrium Unit (LDU) of the polymorphisms described herein can also be used in a similar manner to those described herein. LDUs share an inverse relationship with LD so that regions with high LD (such as haplotype blocks) have few LDUs and low recombination, whilst regions with many LDUs have low LD and high recombination. Methods of calculating LDUs are known in the art (see, e.g., Morton et al., Proc Natl Acad Sci USA 98(9):5217-21 (2001); Tapper et al., Proc Natl Acad Sci USA 102(33):11835-11839 (2005); Maniatis et al., Proc Natl Acad Sci USA 99:2228-2233 (2002)).

Thus, in some embodiments, the methods include analysis of polymorphisms that are within 1 LDU of a polymorphism described herein. Methods are known in the art for identifying such polymorphisms; for example, the International HapMap Project provides a public database that can be used, see hapmap.org, as well as The International HapMap Consortium, Nature 426:789-796 (2003), and The International HapMap Consortium, Nature 437:1299-1320 (2005). Generally, it will be desirable to use a HapMap constructed using data from individuals who share ethnicity with the subject, e.g., a HapMap for African Americans would ideally be used to identify markers within 1 LDU of a marker described herein for use in genotyping a subject of African American descent.

Exemplary polymorphisms that are within 1 LDU of some of the markers described herein are included in the Examples.

Alternatively, methods described herein can include analysis of polymorphisms that are within a value defined by Lewontin's D' (linkage disequilibrium parameter, see Lewontin, Genetics 49:49-67 (1964)) of a polymorphism described herein. Results can be obtained, e.g., from on line public resources such as HapMap.org. The simple linkage disequilibrium parameter (D) reflects the degree to which alleles at two loci (for example two SNPs) occur together more often (positive values) or less often (negative values) than expected in a population as determined by the products of their respective allele frequencies. For any two loci, D can vary in value from −0.25 to +0.25. However, the magnitude of D (Dmax) varies as function of allele frequencies. To control for this, Lewontin introduced the D' parameter, which is D/Dmax and varies in value from −1 (alleles never observed together) to +1 (alleles always observed together). Typically, the absolute value of D' (i.e., |D'|) is reported in online databases, because it follows mathematically that positive association for one set of alleles at two loci corresponds to a negative association of equal magnitude for the reciprocal set. This disequilibrium parameter varies from 0 (no association of alleles at the two loci) to 1 (maximal possible association of alleles at the two loci).

Thus, in some embodiments, the methods include analysis of polymorphisms that are within D'>0.5, D'>0.75, or D'=1, for pairwise comparisons, of a polymorphism described herein.

Identification of Additional Markers for Use in the Methods Described Herein

In general, genetic markers can be identified using any of a number of methods well known in the art. For example, numerous polymorphisms in the regions described herein are known to exist and are available in public databases, which can be searched using methods and algorithms known in the art. Alternately, polymorphisms can be identified by sequencing either genomic DNA or cDNA in the region in which it is desired to find a polymorphism. According to one approach, primers are designed to amplify such a region, and DNA from a subject is obtained and amplified. The DNA is sequenced, and the sequence (referred to as a "subject sequence" or "test sequence") is compared with a reference sequence, which can represent the "normal" or "wild type" sequence, or the "affected" sequence. In some embodiments, a reference sequence can be from, for example, the human draft genome sequence, publicly available in various databases, or a sequence deposited in a database such as GenBank. In some embodiments, the reference sequence is a composite of ethnically diverse individuals.

In general, if sequencing reveals a difference between the sequenced region and the reference sequence, a polymorphism has been identified. The fact that a difference in nucleotide sequence is identified at a particular site that determines that a polymorphism exists at that site. In most instances, particularly in the case of SNPs, only two polymorphic variants will exist at any location. However, in the case of SNPs, up to four variants may exist since there are four naturally occurring nucleotides in DNA. Other polymorphisms, such as insertions and deletions, may have more than four alleles.

Other Genetic Markers of Schizophrenia

The methods described herein can also include determining the presence or absence of other markers known or suspected to be associated with SZ, or with SZ, SD or SPD, e.g., markers outside of a region identified herein, see, e.g., Harrison and Owen, Lancet, 361(9355):417-419 (2003), including, for example, markers on chromosome 22 and other chromosomes, e.g., in the region of 22q12.3 (e.g., near D22S283), 22q11.2, 22q11.2, 22q11-q13, 1q42.1, 1q42.1, 4p, 18p, 15q15, 14q32.3, 13q34, 13q32, 12q24, 11q14-q21, 1q21-q22, 10p15-p13 (e.g., near D10S189), 10q22.3, 8p12-21, 6q13-q26, 6p22.3, 6p23, 5q11.2-q13.3, and/or 3p25. In some embodiments, the methods include determining the presence or absence of one or more other markers that are or may be associated with SZ, or with SZ, SD or SPD, e.g., in one or more genes, e.g., ADRAIA (Clark et al., Biol Psychiatry. 58(6):435-9 (2005)); AKT1 (Emamian et al., Nature Genet. 36:131-137 (2004)); ALDH3B1 (Sun et al. Sci. China C. Life. Sci. 48(3):263-9 (2005)); ARSA (Marcao et al., Mol Genet Metab. 79(4):305-7 (2003); ARVCF (Chen et al., Schizophr Res. 72(2-3):275-7 (2005)); BDNF (Neves-Pereira et al., Molec. Psychiat. 10:208-212 (2005)); BZRP (Kurumaji et al., J Neural Transm. 107(4):491-500 (2000)); DAO (Owen et al., Trends Genet. 21(9):518-25 (2005)); DAOA (Owen et al., 2005, supra); CAPON (Brzustowicz et al., Am J Hum Genet. 74(5): 1057-63 (2004)); CHRNA2 (Blaveri et al., Europ. J. Hum. Genet. 9: 469-472 (2001)); COMT (Shifman et al., Am. J. Hum. Genet. 71:1296-1302 (2002)); CPLX2 (Lee et al., Behav Brain Funct. 1:15 (2005)); DGCR8 (Jacquet et al., Hum Mol Genet. 11(19):2243-9 (2002)); DISC1 (Owen et al., 2005, supra; see, e.g., the D1S2709 marker (Ekelend et al., Hum. Molec. Genet. 10:1611-1617 (2001), HEP3 haplotype, Hennah et al., Hum. Molec. Genet. 12: 3151-3159 (2003), and Leu607Pro, Hodgkinson et al., Am. J. Hum. Genet. 75:862-872 (2004), Erratum: Am. J. Hum. Genet. 76:196 (2005)); DISC2 (Millar et al., Ann Med. 36(5):367-78 (2004)); DPYSL2 (Hong et al., Am J Med Genet B Neuropsychiatr Genet. 136(1):8-11 (2005)); DRD1 (Coon et al., Am. J. Hum. Genet. 52: 327-334 (1993)); DRD2 (Glatt et al., Am. J. Psychiat. 160:469-476 (2003)); DRD3 (Rybakowski et al., Molec. Psychiat. 6:718-724 (2001)); DTNBP1 (Owen et al., 2005, supra); EPSIN4 (Am J Hum Genet. 76(5):902-7 (2005)); ErbB; EGF (Futamura et al., Am. J. Hum. Genet. 52: 327-334 (2002)); GABRA1, GABRA2, GABRA6, GABRP (Petryshen et al., Mol Psychiatry. 10(12):1057 (2005)); GFRA1 (Semba et al., Brain Res Mol Brain Res. 124(1):88-95 (2004)); GNB3 (Kunugi et al., J. Neural Transm. 109(2): 213-8 (2002)); GRIK1 (Shibata et al., Psychiatr Genet. 11(3): 139-44 (2001)); GRIK2 (Shibata et al., Psychiatry Res. 113 (1-2):59-67 (2002)); GRIN1 (Qin et al., Eur J Hum Genet. 13(7):807-14 (2005)); GRIN2A, GRIN2B (Abdolmaleky et al., Am J Pharmacogenomics. 5(3):149-60 (2005)); GRIN2D (Makino et al., Psychiatr Genet. 15(3):215-21 (2005)); GRM3 (Egan et al., Proc Natl Acad Sci U S A. 101(34):

12604-9 (2004)); GRM4 (Ohtsuki et al., Psychiatr Genet. 11(2):79-83 (2001)); G30/G72 (Schulze et al., Am J Psychiatry. 162(11):2101-8 (2005)); HTR2A (Baritaki et al., Eur J Hum Genet. 12(7):535-41 (2004)); HLA-DRB1 (Schwab et al., Am J Med Genet. 114(3):315-20 (2002)); HLA-BRB3 (Yu et al., Zhonghua Liu Xing Bing Xue Za Zhi. 24(9):815-8 (2003)); IL2RB (Schwab et al., Am J Med Genet. 60(5):436-43 (1995)); KCNN3 (Ujike et al., Psychiatry Res. 101(3): 203-7 (2001)); K1F13A (Jamain et al., Genomics. 74(1):36-44 (2001)); KPNA3 (Wei and Hemmings, Neurosci Res. 52(4):342-6 (2005)); LGI1 (Fallin et al. AJ Hum Genet. 77:918-36 (2005)); MAG (Wan et al., Neurosci Lett. 388(3): 126-31 (2005)); MLCI (Verma et al., Biol Psychiatry. 58(1): 16-22 (2005)); MTHFR (Lewis et al., Am. J. Med. Genet. (Neuropsychiat. Genet.) 135B:2-4 (2005)); NOS1 (Liou et al., Schizophr Res. 65(1):57-9 (2003)); NOTCH4 (Wei and Hemmings, (Letter) Nature Genet. 25:376-377 (2000)); NRG1 (Owen et al., 2005, supra); NRG3 (Fallin et al. A J Hum Genet. 77:918-36 (2005)); PCQAP (Sandhu et al., Psychiatr Genet. 14(3):169-72 (2004)); P1K4CA (Saito et al., Am J Med Genet B Neuropsychiatr Genet. 116(1):77-83 (2003)); PLA2G4A, PLA2G4C (Yu et al., Prostaglandins Leukot Essent Fatty Acids. 73(5):351-4 (2005)); PPP3CC (Gerber et al., Proc Natl Acad Sci U S A. 100(15):8993-8 (2003)); PNOC (Blaveri et al., 2001); PRODH (Chakravarti, Proc. Nat. Acad. Sci. 99:4755-4756 (2002)); QKI (Aberg et al., Am J Med Genet B Neuropsychiatr Genet. 2005 Dec. 9; [Epub ahead of print]); RGS4 (Chowdari et al., Hum. Molec. Genet. 11:1373-1380 (2002), Erratum: Hum. Molec. Genet. 12:1781 (2003)); RELN (Costa et al., Mol Interv. 2(1):47-57 (2002)); SCA1 (Culkjovic et al., Am J Med Genet. 96(6): 884-7 (2000)); SLC15A1 (Maheshwari et al., BMC Genomics. 3(1):30 (2002)); SLC18A1 (Bly, Schizophr Res. 78(2-3): 337-8 (2005)); SNAP29 (Saito et al., Mol Psychiatry 6(2): 193-201 (2001); Erratum in: Mol Psychiatry 6(5):605 (2001); SYNGR1 (Verma et al., Biol Psychiatry. 55(2):196-9 (2004)); SYN2 (Chen et al., Bio. Psychiat. 56:177-181 (2004)); SYN3 (Porton et al. Biol Psychiatry. 55(2):118-25 (2004)); TBP/SCA17 (Chen et al., Schizophr Res. 78(2-3): 131-6 (2005)); TPP2 (Fallin et al. AJ Hum Genet. 77:918-36 (2005)); TRAR4 (Am J Hum Genet. 75(4):624-38 (2004)); TRAX (Thomson et al., Mol Psychiatry. 10(7):657-68, 616 (2005)); UFD1L (De Luca et al., Am J Med Genet. 105(6): 529-33 (2001)); YWHAH (Toyooka et al., Am J Med Genet. 88(2):164-7 (1999)); ZDHHC8 (Mukai et al., Nature Genet. 36:725-731 (2004)); or ZNF74 (Takase et al., Schizophr Res. 52(3):161-5 (2001)). See also, e.g., OMIM entry no. 181500 (SCZD).

Methods of Determining the Presence or Absence of a Haplotype Associated with SZ, SPD or SD The methods described herein include determining the presence or absence of haplotypes associated with SZ, SPD or SD. In some embodiments, an association with SZ is determined by the presence of a shared haplotype between the subject and an affected reference individual, e.g., a first or second-degree relation of the subject, and the absence of the haplotype in an unaffected reference individual. Thus the methods can include obtaining and analyzing a sample from a suitable reference individual.

Samples that are suitable for use in the methods described herein contain genetic material, e.g., genomic DNA (gDNA). Non-limiting examples of sources of samples include urine, blood, and tissue. The sample itself will typically consist of nucleated cells (e.g., blood or buccal cells), tissue, etc., removed from the subject. The subject can be an adult, child, fetus, or embryo. In some embodiments, the sample is obtained prenatally, either from a fetus or embryo or from the mother (e.g., from fetal or embryonic cells in the maternal circulation). Methods and reagents are known in the art for obtaining, processing, and analyzing samples. In some embodiments, the sample is obtained with the assistance of a health care provider, e.g., to draw blood. In some embodiments, the sample is obtained without the assistance of a health care provider, e.g., where the sample is obtained non-invasively, such as a sample comprising buccal cells that is obtained using a buccal swab or brush, or a mouthwash sample.

The sample may be further processed before the detecting step. For example, DNA in a cell or tissue sample can be separated from other components of the sample. The sample can be concentrated and/or purified to isolate DNA. Cells can be harvested from a biological sample using standard techniques known in the art. For example, cells can be harvested by centrifuging a cell sample and resuspending the pelleted cells. The cells can be resuspended in a buffered solution such as phosphate-buffered saline (PBS). After centrifuging the cell suspension to obtain a cell pellet, the cells can be lysed to extract DNA, e.g., gDNA. See, e.g., Ausubel et al., 2003, supra. All samples obtained from a subject, including those subjected to any sort of further processing, are considered to be obtained from the subject.

The absence or presence of a haplotype associated with SZ, SPD or SD as described herein can be determined using methods known in the art, e.g., gel electrophoresis, capillary electrophoresis, size exclusion chromatography, sequencing, and/or arrays to detect the presence or absence of the marker(s) of the haplotype. Amplification of nucleic acids, where desirable, can be accomplished using methods known in the art, e.g., PCR.

Methods of nucleic acid analysis to detect polymorphisms and/or polymorphic variants include, e.g., microarray analysis. Hybridization methods, such as Southern analysis, Northern analysis, or in situ hybridizations, can also be used (see *Current Protocols in Molecular Biology*, Ausubel, F. et al., eds., John Wiley & Sons 2003). To detect microdeletions, fluorescence in situ hybridization (FISH) using DNA probes that are directed to a putatively deleted region in a chromosome can be used. For example, probes that detect all or a part of microsatellite marker D22s526 can be used to detect microdeletions in the region that contains that marker.

Other methods include direct manual sequencing (Church and Gilbert, Proc. Natl. Acad. Sci. USA 81:1991-1995 (1988); Sanger et al., Proc. Natl. Acad. Sci. 74:5463-5467 (1977); Beavis et al. U.S. Pat. No. 5,288,644); automated fluorescent sequencing; single-stranded conformation polymorphism assays (SSCP); clamped denaturing gel electrophoresis (CDGE); two-dimensional gel electrophoresis (2DGE or TDGE); conformational sensitive gel electrophoresis (CSGE); denaturing gradient gel electrophoresis (DGGE) (Sheffield et al., Proc. Natl. Acad. Sci. USA 86:232-236 (1989)), mobility shift analysis (Orita et al., Proc. Natl. Acad. Sci. USA 86:2766-2770 (1989)), restriction enzyme analysis (Flavell et al., Cell 15:25 (1978); Geever et al., Proc. Natl. Acad. Sci. USA 78:5081 (1981)); quantitative real-time PCR (Raca et al., Genet Test 8(4):387-94 (2004)); heteroduplex analysis; chemical mismatch cleavage (CMC) (Cotton et al., Proc. Natl. Acad. Sci. USA 85:4397-4401 (1985)); RNase protection assays (Myers et al., Science 230:1242 (1985)); use of polypeptides that recognize nucleotide mismatches, e.g., *E. coli* mutS protein; allele-specific PCR, for example. See, e.g., U.S. Patent Publication No. 2004/0014095, to Gerber et al., which is incorporated herein by reference in its entirety. In some embodiments, the methods described herein include determining the sequence of the entire region of 22q13 described herein as being of interest, e.g., between and including SNPs rs738596, rs738598, or rs135221 on the proximal end, and rs13884 or rs137853 on the distal end. In some embodiments, the sequence is determined on both strands of DNA.

In order to detect polymorphisms and/or polymorphic variants, it will frequently be desirable to amplify a portion of genomic DNA (gDNA) encompassing the polymorphic site. Such regions can be amplified and isolated by PCR using oligonucleotide primers designed based on genomic and/or cDNA sequences that flank the site. See e.g., *PCR Primer: A Laboratory Manual*, Dieffenbach and Dveksler, (Eds.); McPherson et al., *PCR Basics: From Background to Bench* (Springer Verlag, 2000); Mattila et al., Nucleic Acids Res., 19:4967 (1991); Eckert et al., *PCR Methods and Applications*, 1:17 (1991); *PCR* (eds. McPherson et al., IRL Press, Oxford); and U.S. Pat. No. 4,683,202. Other amplification methods that may be employed include the ligase chain reaction (LCR) (Wu and Wallace, Genomics, 4:560 (1989), Landegren et al., Science, 241:1077 (1988), transcription amplification (Kwoh et al., Proc. Natl. Acad. Sci. USA, 86:1173 (1989)), self-sustained sequence replication (Guatelli et al., Proc. Nat. Acad. Sci. USA, 87:1874 (1990)), and nucleic acid based sequence amplification (NASBA). Guidelines for selecting primers for PCR amplification are well known in the art. See, e.g., McPherson et al., *PCR Basics: From Background to Bench*, Springer-Verlag, 2000. A variety of computer programs for designing primers are available, e.g., 'Oligo' (National Biosciences, Inc, Plymouth Minn.), MacVector (Kodak/IBI), and the GCG suite of sequence analysis programs (Genetics Computer Group, Madison, Wis. 53711).

In one example, a sample (e.g., a sample comprising genomic DNA), is obtained from a subject. The DNA in the sample is then examined to determine a haplotype as described herein. The haplotype can be determined by any method described herein, e.g., by sequencing or by hybridization of the gene in the genomic DNA, RNA, or cDNA to a nucleic acid probe, e.g., a DNA probe (which includes cDNA and oligonucleotide probes) or an RNA probe. The nucleic acid probe can be designed to specifically or preferentially hybridize with a particular polymorphic variant.

In some embodiments, a peptide nucleic acid (PNA) probe can be used instead of a nucleic acid probe in the hybridization methods described above. PNA is a DNA mimetic with a peptide-like, inorganic backbone, e.g., N-(2-aminoethyl)glycine units, with an organic base (A, G, C, T or U) attached to the glycine nitrogen via a methylene carbonyl linker (see, e.g., Nielsen et al., *Bioconjugate Chemistry*, The American Chemical Society, 5:1 (1994)). The PNA probe can be designed to specifically hybridize to a nucleic acid comprising a polymorphic variant conferring susceptibility to or indicative of the presence of SZ.

In some embodiments, restriction digest analysis can be used to detect the existence of a polymorphic variant of a polymorphism, if alternate polymorphic variants of the polymorphism result in the creation or elimination of a restriction site. A sample containing genomic DNA is obtained from the individual. Polymerase chain reaction (PCR) can be used to amplify a region comprising the polymorphic site, and restriction fragment length polymorphism analysis is conducted (see Ausubel et al., *Current Protocols in Molecular Biology*, supra). The digestion pattern of the relevant DNA fragment indicates the presence or absence of a particular polymorphic variant of the polymorphism and is therefore indicative of the presence or absence of susceptibility to Sz.

Sequence analysis can also be used to detect specific polymorphic variants. A sample comprising DNA or RNA is obtained from the subject. PCR or other appropriate methods can be used to amplify a portion encompassing the polymorphic site, if desired. The sequence is then ascertained, using any standard method, and the presence of a polymorphic variant is determined.

Allele-specific oligonucleotides can also be used to detect the presence of a polymorphic variant, e.g., through the use of dot-blot hybridization of amplified oligonucleotides with allele-specific oligonucleotide (ASO) probes (see, for example, Saiki et al., Nature (London) 324:163-166 (1986)). An "allele-specific oligonucleotide" (also referred to herein as an "allele-specific oligonucleotide probe") is typically an oligonucleotide of approximately 10-50 base pairs, preferably approximately 15-30 base pairs, that specifically hybridizes to a nucleic acid region that contains a polymorphism. An allele-specific oligonucleotide probe that is specific for particular a polymorphism can be prepared using standard methods (see Ausubel et al., *Current Protocols in Molecular Biology*, supra).

Generally, to determine which of multiple polymorphic variants is present in a subject, a sample comprising DNA is obtained from the individual. PCR can be used to amplify a portion encompassing the polymorphic site. DNA containing the amplified portion may be dot-blotted, using standard methods (see Ausubel et al., *Current Protocols in Molecular Biology*, supra), and the blot contacted with the oligonucleotide probe. The presence of specific hybridization of the probe to the DNA is then detected. Specific hybridization of an allele-specific oligonucleotide probe (specific for a polymorphic variant indicative of susceptibility to SZ) to DNA from the subject is indicative of susceptibility to SZ.

In some embodiments, fluorescence polarization template-directed dye-terminator incorporation (FP-TDI) is used to determine which of multiple polymorphic variants of a polymorphism is present in a subject (Chen et al., (1999) Genome Research, 9(5):492-498). Rather than involving use of allele-specific probes or primers, this method employs primers that terminate adjacent to a polymorphic site, so that extension of the primer by a single nucleotide results in incorporation of a nucleotide complementary to the polymorphic variant at the polymorphic site.

Real-time pyrophosphate DNA sequencing is yet another approach to detection of polymorphisms and polymorphic variants (Alderborn et al., (2000) Genome Research, 10(8): 1249-1258). Additional methods include, for example, PCR amplification in combination with denaturing high performance liquid chromatography (dHPLC) (Underhill, P. A., et al., Genome Research, Vol. 7, No. 10, pp. 996-1005, 1997).

The methods can include determining the genotype of a subject with respect to both copies of the polymorphic site present in the genome. For example, the complete genotype may be characterized as −/−, as −/+, or as +/+, where a minus sign indicates the presence of the reference or wild type sequence at the polymorphic site, and the plus sign indicates the presence of a polymorphic variant other than the reference sequence. If multiple polymorphic variants exist at a site, this can be appropriately indicated by specifying which ones are present in the subject. Any of the detection means described herein can be used to determine the genotype of a subject with respect to one or both copies of the polymorphism present in the subject's genome.

In some embodiments, it is desirable to employ methods that can detect the presence of multiple polymorphisms (e.g., polymorphic variants at a plurality of polymorphic sites) in parallel or substantially simultaneously. Oligonucleotide arrays represent one suitable means for doing so. Other methods, including methods in which reactions (e.g., amplification, hybridization) are performed in individual vessels, e.g., within individual wells of a multi-well plate or other vessel may also be performed so as to detect the presence of multiple polymorphic variants (e.g., polymorphic variants at a plurality of polymorphic sites) in parallel or substantially simultaneously according to certain embodiments of the invention.

Probes

Nucleic acid probes can be used to detect and/or quantify the presence of a particular target nucleic acid sequence within a sample of nucleic acid sequences, e.g., as hybridization probes, or to amplify a particular target sequence within a sample, e.g., as a primer. Probes have a complimentary nucleic acid sequence that selectively hybridizes to the target nucleic acid sequence. In order for a probe to hybridize to a target sequence, the hybridization probe must have sufficient identity with the target sequence, i.e., at least 70%, e.g., 80%, 90%, 95%, 98% or more identity to the target sequence. The probe sequence must also be sufficiently long so that the probe exhibits selectivity for the target sequence over non-target sequences. For example, the probe will be at least 20, e.g., 25, 30, 35, 50, 100, 200, 300, 400, 500, 600, 700, 800, 900 or more, nucleotides in length. In some embodiments, the probes are not more than 30, 50, 100, 200, 300, 500, 750, or 1000 nucleotides in length. Probes are typically about 20 to about $1 \times 10^6$ nucleotides in length. Probes include primers, which generally refers to a single-stranded oligonucleotide probe that can act as a point of initiation of template-directed DNA synthesis using methods such as PCR (polymerase chain reaction), LCR (ligase chain reaction), etc., for amplification of a target sequence.

In some embodiments, the probe is a test probe, e.g., a probe that can be used to detect polymorphisms in a region described herein, e.g., polymorphisms as described herein, including D22S526, D22S1749E, and/or other polymorphisms of the Sult4a1 gene lying between SNP markers rs138060 and rs138110. In some embodiments, the probe can hybridize to a target sequence within a region delimited by SNP rs738596 and SNP rs743615 (described on the internet at ncbi.nlm.nih.gov/SNP/snp_ref.cgi?rs=738596 and ncbi.nlm.nih.gov/SNP/snp_ref.cgi?rs=743615, respectively).

In some embodiments, the probe can bind to another marker sequence associated with SZ, SPD or SD, as described herein.

Control probes can also be used. For example, a probe that binds a less variable sequence, e.g., repetitive DNA associated with a centromere of a chromosome, can be used as a control. Probes that hybridize with various centromeric DNA and locus-specific DNA are available commercially, for example, from Vysis, Inc. (Downers Grove, Ill.), Molecular Probes, Inc. (Eugene, Oreg.), or from Cytocell (Oxfordshire, UK). Probe sets are available commercially, e.g., from Applied Biosystems, e.g., the Assays-on-Demand SNP kits Alternatively, probes can be synthesized, e.g., chemically or in vitro, or made from chromosomal or genomic DNA through standard techniques. For example, sources of DNA that can be used include genomic DNA, cloned DNA sequences, somatic cell hybrids that contain one, or a part of one, human chromosome along with the normal chromosome complement of the host, and chromosomes purified by flow cytometry or microdissection. The region of interest can be isolated through cloning, or by site-specific amplification via the polymerase chain reaction (PCR). See, for example, Nath and Johnson, Biotechnic. Histochem., 1998, 73(1):6-22, Wheeless et al., Cytometry 1994, 17:319-326, and U.S. Pat. No. 5,491,224.

In some embodiments, the probes are labeled, e.g., by direct labeling, with a fluorophore, an organic molecule that fluoresces after absorbing light of lower wavelength/higher energy. A directly labeled fluorophore allows the probe to be visualized without a secondary detection molecule. After covalently attaching a fluorophore to a nucleotide, the nucleotide can be directly incorporated into the probe with standard techniques such as nick translation, random priming, and PCR labeling. Alternatively, deoxycytidine nucleotides within the probe can be transaminated with a linker. The fluorophore then is covalently attached to the transaminated deoxycytidine nucleotides. See, e.g., U.S. Pat. No. 5,491,224.

Fluorophores of different colors can be chosen such that each probe in a set can be distinctly visualized. For example, a combination of the following fluorophores can be used: 7-amino-4-methylcoumarin-3-acetic acid (AMCA), Texas Red™ (Molecular Probes, Inc., Eugene, Oreg.), 5-(and-6)-carboxy-X-rhodamine, lissamine rhodamine B, 5-(and-6)-carboxyfluorescein, fluorescein-5-isothiocyanate (FITC), 7-diethylaminocoumarin-3-carboxylic acid, tetramethylrhodamine-5-(and-6)-isothiocyanate, 5-(and-6)-carboxytetramethylrhodamine, 7-hydroxycoumarin-3-carboxylic acid, 6-[fluorescein 5-(and-6)-carboxamido]hexanoic acid, N-(4, 4-difluoro-5,7-dimethyl-4-bora-3a, 4a diaza-3-indacenepropionic acid, eosin-5-isothiocyanate, erythrosin-5-isothiocyanate, and Cascade™ blue acetylazide (Molecular Probes, Inc., Eugene, Oreg.). Fluorescently labeled probes can be viewed with a fluorescence microscope and an appropriate filter for each fluorophore, or by using dual or triple band-pass filter sets to observe multiple fluorophores. See, for example, U.S. Pat. No. 5,776,688. Alternatively, techniques such as flow cytometry can be used to examine the hybridization pattern of the probes. Fluorescence-based arrays are also known in the art.

In other embodiments, the probes can be indirectly labeled with, e.g., biotin or digoxygenin, or labeled with radioactive isotopes such as $^{32}P$ and $^3H$. For example, a probe indirectly labeled with biotin can be detected by avidin conjugated to a detectable marker. For example, avidin can be conjugated to an enzymatic marker such as alkaline phosphatase or horseradish peroxidase. Enzymatic markers can be detected in standard calorimetric reactions using a substrate and/or a catalyst for the enzyme. Catalysts for alkaline phosphatase include 5-bromo-4-chloro-3-indolylphosphate and nitro blue tetrazolium. Diaminobenzoate can be used as a catalyst for horseradish peroxidase.

Oligonucleotide probes that exhibit differential or selective binding to polymorphic sites may readily be designed by one of ordinary skill in the art. For example, an oligonucleotide that is perfectly complementary to a sequence that encompasses a polymorphic site (i.e., a sequence that includes the polymorphic site, within it or at one end) will generally hybridize preferentially to a nucleic acid comprising that sequence, as opposed to a nucleic acid comprising an alternate polymorphic variant.

Arrays and Uses Thereof

In another aspect, the invention features arrays that include a substrate having a plurality of addressable areas, and methods of using them. At least one area of the plurality includes a nucleic acid probe that binds specifically to a sequence in chromosome 22q13, and can be used to detect the absence or presence of a polymorphism, e.g., one or more SNPs, microsatellites, minisatellites, or indels, as described herein, to determine a haplotype in this region. For example, the array can include one or more nucleic acid probes that can be used to detect a polymorphism listed in table 4, 6, 7, 8, or 9. In some embodiments, the array further includes at least one area that includes a nucleic acid probe that can be used to specifically detect another marker associated with SZ, SPD or SD, as described herein. The substrate can be, e.g., a two-dimensional substrate known in the art such as a glass slide, a wafer (e.g., silica or plastic), a mass spectroscopy plate, or a three-dimensional substrate such as a gel pad. In some embodiments, the probes are nucleic acid capture probes.

Methods for generating arrays are known in the art and include, e.g., photolithographic methods (see, e.g., U.S. Pat. Nos. 5,143,854; 5,510,270; and 5,527,681), mechanical methods (e.g., directed-flow methods as described in U.S. Pat. No. 5,384,261), pin-based methods (e.g., as described in U.S. Pat. No. 5,288,514), and bead-based techniques (e.g., as described in PCT US/93/04145). The array typically includes oligonucleotide probes capable of specifically hybridizing to different polymorphic variants. According to the method, a nucleic acid of interest, e.g., a nucleic acid encompassing a polymorphic site, (which is typically amplified) is hybridized with the array and scanned. Hybridization and scanning are generally carried out according to standard methods. See, e.g., Published PCT Application Nos. WO 92/10092 and WO 95/11995, and U.S. Pat. No. 5,424,186. After hybridization and washing, the array is scanned to determine the position on the array to which the nucleic acid hybridizes. The hybridization data obtained from the scan is typically in the form of fluorescence intensities as a function of location on the array.

Arrays can include multiple detection blocks (i.e., multiple groups of probes designed for detection of particular polymorphisms). Such arrays can be used to analyze multiple different polymorphisms. Detection blocks may be grouped within a single array or in multiple, separate arrays so that varying conditions (e.g., conditions optimized for particular polymorphisms) may be used during the hybridization. For example, it may be desirable to provide for the detection of those polymorphisms that fall within G-C rich stretches of a genomic sequence, separately from those falling in A-T rich segments. Additional description of use of oligonucleotide arrays for detection of polymorphisms can be found, for example, in U.S. Pat. Nos. 5,858,659 and 5,837,832. In addition to oligonucleotide arrays, cDNA arrays may be used similarly in certain embodiments of the invention.

The methods described herein can include providing an array as described herein; contacting the array with a sample, e.g., a portion of genomic DNA that includes at least a portion of human chromosome 22, e.g., a region between SNP rs738596 and SNP rs743615, and, optionally, a different portion of genomic DNA, e.g., a portion that includes a different portion of human chromosome 22 or another chromosome, e.g., including another region associated with SZ, SPD or SD., and detecting binding of a nucleic acid from the sample to the array. Optionally, the method includes amplifying nucleic acid from the sample, e.g., genomic DNA that includes a portion of human chromosome 22q13 described herein, and, optionally, a region that includes another region associated with SZ, SPD, or SD, prior to or during contact with the array.

In some aspects, the methods described herein can include using an array that can ascertain differential expression patterns or copy numbers of one or more genes in samples from normal and affected individuals. For example, arrays of probes to a marker described herein can be used to measure polymorphisms between DNA from a subject having SZ, SPD, or SD, and control DNA, e.g., DNA obtained from an individual that does not have SZ, SPD, or SD, and has no risk factors for SZ, SPD, or SD. Since the clones on the array contain sequence tags, their positions on the array are accurately known relative to the genomic sequence. Different hybridization patterns between DNA from an individual afflicted with SZ and DNA from a normal individual at areas in the array corresponding to markers in human chromosome 22q13 described herein, and, optionally, one or more other regions associated with SZ, SPD, or SD, are indicative of a risk of SZ. Methods for array production, hybridization, and analysis are described, e.g., in Snijders et al., (2001) *Nat. Genetics* 29:263-264; Klein et al., (1999) Proc. Natl Acad. Sci. U.S.A. 96:4494-4499; Albertson et al., (2003) Breast Cancer Research and Treatment 78:289-298; and Snijders et al. "BAC microarray based comparative genomic hybridization." In: Zhao et al. (eds), *Bacterial Artificial Chromosomes: Methods and Protocols*, Methods in Molecular Biology, Humana Press, 2002.

In another aspect, the invention features methods of determining the absence or presence of a haplotype associated with SZ as described herein, using an array described above. The methods include providing a two dimensional array having a plurality of addresses, each address of the plurality being positionally distinguishable from each other address of the plurality having a unique nucleic acid capture probe, contacting the array with a first sample from a test subject who is suspected of having or being at risk for SZ, and comparing the binding of the first sample with one or more references, e.g., binding of a sample from a subject who is known to have SZ, SPD, or SD, and/or binding of a sample from a subject who is unaffected, e.g., a control sample from a subject who neither has, nor has any risk factors for SZ, SPD, or SD. In some embodiments, the methods include contacting the array with a second sample from a subject who has SZ, SPD or SD; and comparing the binding of the first sample with the binding of the second sample. In some embodiments, the methods include contacting the array with a third sample from a cell or subject that does not have SZ and is not at risk for SZ; and comparing the binding of the first sample with the binding of the third sample. In some embodiments, the second and third samples are from first or second-degree relatives of the test subject. Binding, e.g., in the case of a nucleic acid hybridization, with a capture probe at an address of the plurality, can be detected by any method known in the art, e.g., by detection of a signal generated from a label attached to the nucleic acid.

Schizophrenia, Schizotypal Personality Disorder, and Schizoaffective Disorder

The methods described herein can be used to determine an individual's risk of developing schizophrenia (SZ), schizotypal personality disorder (SPD), and/or a schizoaffective disorder (SD).

Schizophrenia (SZ)

SZ is considered a clinical syndrome, and is probably a constellation of several pathologies. Substantial heterogeneity is seen between cases, which is thought to reflect multiple overlapping etiologic factors, including both genetic and environmental contributions. A diagnosis of SZ is typically indicated by chronic psychotic symptoms, e.g., hallucinations and delusions. Disorganization of thought and behavior are common and are considered distinguishing factors in the diagnosis of SZ. Patients typically have some subtle impairments in cognition. Reduced emotional experience and expression, low drive, and impaired speech are observed in a subgroup of patients. Cognitive, emotional and social impairments often appear early in life, while the psychotic symptoms typically manifest in late adolescence or early adulthood in men, a little later in women.

A diagnosis of SZ can be made according to the criteria reported in the *Diagnostic and Statistical Manual of Mental Disorders Fourth Edition, Text Revision*, American Psychiatric Association, 2000, (referred to herein as DSM-IV) as follows:

Diagnostic Criteria for SZ

All six criteria must be met for a diagnosis of SZ.

A. Characteristic symptoms: Two (or more) of the following, each present for a significant portion of time during a one month period (or less if successfully treated):

(1) delusions
(2) hallucinations
(3) disorganized speech (e.g., frequent derailment or incoherence)
(4) grossly disorganized or catatonic behavior
(5) negative symptoms, e.g., affective flattening, alogia, or avolition Only one criterion A symptom is required if delusions are bizarre or hallucinations consist of a voice keeping up a running commentary on the person's behavior or thoughts, or two or more voices conversing with each other.

B. Social/occupational dysfunction: For a significant portion of the time since the onset of the disturbance, one or more major areas of functioning such as work, interpersonal relations, or self-care are markedly below the level achieved prior to the onset (or when the onset is in childhood or adolescence, failure to achieve expected level of interpersonal, academic, or occupational achievement).

C. Duration: Continuous signs of the disturbance persist for at least 6 months. This 6-month period must include at least 1 month of symptoms (or less if successfully treated) that meet Criterion A (i.e., active-phase symptoms) and may include periods of prodromal or residual symptoms. During these prodromal or residual periods, the signs of the disturbance may be manifested by only negative symptoms or two or more symptoms listed in Criterion A present in an attenuated form (e.g., odd beliefs, unusual perceptual experiences).

D. Schizoaffective and Mood Disorder Exclusion: Schizoaffective Disorder and Mood Disorder With Psychotic Features have been ruled out because either (1) no major depressive, manic, or mixed episodes have occurred concurrently with the active-phase symptoms; or (2) if mood episodes have occurred during active-phase symptoms, their total duration has been brief relative to the duration of the active and residual periods.

E. Substance/General Medical Condition Exclusion: The disturbance is not due to the direct physiological effects of a substance (e.g., a drug of abuse, a medication) or a general medical condition.

F. Relationship to a Pervasive Developmental Disorder: If the patient has a history of Autistic Disorder or another Pervasive Developmental Disorder, the additional diagnosis of SZ is made only if prominent delusions or hallucinations are also present for at least a month (or less if successfully treated).

Schizoaffective Disorder (SD)

SD is characterized by the presence of affective (depressive or manic) symptoms and schizophrenic symptoms within the same, uninterrupted episode of illness.

Diagnostic Criteria for Schizoaffective Disorder

The DSM-IV Criteria for a diagnosis of schizoaffective disorder is as follows:

An uninterrupted period of illness during which, at some time, there is either (1) a Major Depressive Episode (which must include depressed mood), (2) a Manic Episode, or (3) a Mixed Episode, concurrent with symptoms that meet (4) Criterion A for SZ, above.

A. Criteria for Major Depressive Episode

At least five of the following symptoms must be present during the same 2-week period and represent a change from previous functioning; at least one of the symptoms is either (1) depressed mood or (2) loss of interest or pleasure.

(1) depressed mood most of the day, nearly every day, as indicated by either subjective report (e.g., feels sad or empty) or observation made by others (e.g., appears tearful). In children and adolescents, this can be an irritable mood.

(2) markedly diminished interest or pleasure in all, or almost all, activities most of the day, nearly every day (as indicated by either subjective account or observation made by others)

(3) significant weight loss when not dieting or weight gain (e.g., a change of more than 5% of body weight in a month), or decrease or increase in appetite nearly every day. (In children, failure to make expected weight gains is considered).

(4) insomnia or hypersomnia nearly every day (5) psychomotor agitation or retardation nearly every day (observable by others, not merely subjective feelings of restlessness or being slowed down)

(6) fatigue or loss of energy nearly every day (7) feelings of worthlessness or excessive or inappropriate guilt (which may be delusional) nearly every day (not merely self-reproach or guilt about being sick)

(8) diminished ability to think or concentrate, or indecisiveness, nearly every day (either by subjective account or as observed by others)

(9) recurrent thoughts of death (not just fear of dying), recurrent suicidal ideation without a specific plan, or a suicide attempt or a specific plan for committing suicide In addition, the symptoms do not meet criteria for a Mixed Episode. The symptoms cause clinically significant distress or impairment in social, occupational, or other important areas of functioning. The symptoms are not due to the direct physiological effects of a substance (e.g., a drug of abuse, a medication) or a general medical condition (e.g., hypothyroidism).

The symptoms are not better accounted for by Bereavement, i.e., after the loss of a loved one, the symptoms persist for longer than 2 months, or are characterized by marked functional impairment, morbid preoccupation with worthlessness, suicidal ideation, psychotic symptoms, or psychomotor retardation.

B. Criteria for Manic Episode

A manic episode is a distinct period of abnormally and persistently elevated, expansive, or irritable mood, lasting at least one week (or any duration, if hospitalization is necessary).

During the period of mood disturbance, three (or more) of the following symptoms have persisted (four if the mood is only irritable) and have been present to a significant degree:

(1) inflated self-esteem or grandiosity
(2) decreased need for sleep (e.g., feels rested after only 3 hours of sleep)
(3) more talkative than usual or pressure to keep talking
(4) flight of ideas or subjective experience that thoughts are racing
(5) distractibility (i.e., attention too easily drawn to unimportant or irrelevant external stimuli)
(6) increase in goal-directed activity (either socially, at work or school, or sexually) or psychomotor agitation
(7) excessive involvement in pleasurable activities that have a high potential for painful consequences (e.g., engaging in unrestrained buying sprees, sexual indiscretions, or foolish business investments)

The symptoms do not meet criteria for a Mixed Episode. The mood disturbance is sufficiently severe to cause marked impairment in occupational functioning or in usual social activities or relationships with others, or to necessitate hospitalization to prevent harm to self or others, or there are psychotic features. The symptoms are not due to the direct physiological effects of a substance (e.g., a drug of abuse, a medication, or other treatment) or a general medical condition (e.g., hyperthyroidism).

C. Criteria for Mixed Episode

A mixed episode occurs when the criteria are met both for a Manic Episode and for a Major Depressive Episode (except for duration) nearly every day during at least a 1-week period. The mood disturbance is sufficiently severe to cause marked impairment in occupational functioning or in usual social activities or relationships with others, or to necessitate hospitalization to prevent harm to self or others, or there are psychotic features.

The symptoms are not due to the direct physiological effects of a substance (e.g., a drug of abuse, a medication, or other treatment) or a general medical condition (e.g., hyperthyroidism).

D. Criterion A of SZ

See above.

E. Types of SD

The type of SD may be may be specifiable, as either Bipolar Type, if the disturbance includes a Manic or a Mixed Episode (or a Manic or a Mixed Episode and Major Depressive Episodes), or Depressive Type, if the disturbance only includes Major Depressive Episodes.

F. Associated Features

Features associated with SD include Learning Problems, Hypoactivity, Psychotic, Euphoric Mood, Depressed Mood, Somatic/Sexual Dysfunction, Hyperactivity, Guilt/Obsession, Odd/Eccentric/Suspicious Personality, Anxious/Fearful/Dependent Personality, and Dramatic/Erratic/Antisocial Personality.

Schizotypal Personality Disorder (SPD)

Diagnostic Criteria for SPD

A diagnosis of SPD under the criteria of the DSM-IV is generally based on a pervasive pattern of social and interpersonal deficits marked by acute discomfort with, and reduced capacity for, close relationships as well as by cognitive or perceptual distortions and eccentricities of behavior, beginning by early adulthood and present in a variety of contexts, as indicated by five (or more) of the following:

(1) ideas of reference (excluding delusions of reference)

(2) odd beliefs or magical thinking that influences behavior and is (3) inconsistent with subcultural norms (e.g., superstitiousness, belief in clairvoyance, telepathy, or "sixth sense;" in children and adolescents, bizarre fantasies or preoccupations)

(4) unusual perceptual experiences, including bodily illusions (5) odd thinking and speech (e.g., vague, circumstantial, metaphorical, overelaborate, or stereotyped)

(6) suspiciousness or paranoid ideation (7) inappropriate or constricted affect (8) behavior or appearance that is odd, eccentric, or peculiar (9) lack of close friends or confidants other than first-degree relatives

(10) excessive social anxiety that does not diminish with familiarity and tends to be associated with paranoid fears rather than negative judgments about self SPD is diagnosed if the symptoms do not occur exclusively during the course of SZ, a Mood Disorder With Psychotic Features, another Psychotic Disorder, or a Pervasive Developmental Disorder, and the disturbance is not due to the direct physiological effects of a substance (e.g., a drug of abuse, a medication) or a general medical condition.

Associated features of SPD include Depressed Mood and Odd/Eccentric/Suspicious Personality.

Endophenotypes in SZ

A number of endophenotypes, i.e., intermediate phenotypes, that may more closely reflect biological mechanisms behind SZ, have been suggested, such as prepulse inhibition, structural abnormalities evident in MRI scans, specific domains of cognition (e.g., executive function), fine motor performance, working memory, etc.

Endophenotypes can also include clinical manifestations such as hallucinations, paranoia, mania, depression, obsessive-compulsive symptoms, etc., as well as response or lack of response to drugs and comorbidity for substance and alcohol abuse.

See, e.g., Kendler et al., Am J Psychiatry 152(5):749-54 (1995); Gottesman and Gould, Am J Psychiatry 160(4):636-45 (2003); Cadenhead, Psychiatric Clinics of North America. 25(4):837-53 (2002); Gottesman and Gould, American Journal of Psychiatry. 160(4):636-45 (2003); Heinrichs, Neuroscience & Biobehavioral Reviews. 28(4):379-94 (2004); and Zobel and Maier, Nervenarzt. 75(3):205-14 (2004).

There is now evidence that some candidate genes that were identified using DSM-IV type categorical definitions for "affected" individuals may influence specific endophenotypes, see, e.g., Baker et al., Biol Psychiatry 58(1):23-31 (2005); Cannon et al., Arch Gen Psychiatry 62(11):1205-13 (2005); Gothelf et al., Nat Neurosci 8(11):1500-2 (2005); Hallmayer et al., Am J Hum Genet 77(3):468-76 (2005); Callicott et al., Proc Natl Acad Sci U S A 102(24):8627-32 (2005); Gomick et al., J Autism Dev Disord 1-8 (2005). Thus, the methods described herein can be used to associate haplotypes of 22q13 with specific endophenotypes.

Current Treatment of SZ, SD, or SPD

Subjects with SZ typically require acute treatment for psychotic exacerbations, and long-term treatment including maintenance and prophylactic strategies to sustain symptom improvement and prevent recurrence of psychosis. Subjects with schizoaffective disorder experience the symptoms of both SZ and affective disorder (manic and/or depressive), thus require the specific treatments for each disorder. Subjects with SPD sometimes require medication for acute psychotic episodes but are often treated using psychosocial methods. The methods described herein can include the administration of one or more accepted or experimental treatment modalities to a person identified as at risk of developing SZ, SPD, or a SD, based on the presence of a haplotype associated with SZ, SPD, or SD. Currently accepted treatments presently include both pharmacologic and psychosocial management, and occasionally electroconvulsive therapy (ECT).

Standard pharmacologic therapies for SZ and SD include the administration of one or more antipsychotic medications, which are typically antagonists acting at postsynaptic $D_2$ dopamine receptors in the brain. Antipsychotic medications include conventional, or first generation, antipsychotic agents, which are sometimes referred to as neuroleptics because of their neurologic side effects, and second generation antipsychotic agents, which are less likely to exhibit neuroleptic effects and have been termed atypical antipsychotics.

In some embodiments, the methods described herein include the administration of one or more antipsychotic medications to a person identified by a method described herein as being at risk of developing SZ, SPD, or SD. Antipsychotic medications substantially reduce the risk of relapse in the stable phase of illness. In some embodiments, the methods include the administration of a first generation antipsychotic medication at a dose that is around the "extrapyramidal symptom (EPS) threshold" (i.e., the dose that will induce extrapyramidal side effects, e.g., bradykinesia, rigidity, or dyskinesia, with minimal rigidity detectable on physical examination, and/or a second-generation antipsychotics at a dose that is therapeutic, yet below the EPS threshold.

Standard pharmacologic therapies for SD also include the administration of a combination of antidepressant, and anti-anxiety medication. Suitable antidepressants include serotonergic antidepressants, e.g., fluoxetine or trazodone. Suitable anxiolytics include benzodiazepines, e.g., lorazepam, clonazepam. Lithium can also be administered. Thus, in some embodiments, the methods can include the administration of one or more antidepressant and/or anti-anxiety medications to a person identified as at risk of developing SZ, SPD, or SD.

The methods can also include psychosocial and rehabilitation interventions, e.g., interventions that are generally accepted as therapeutically beneficial, e.g., cognitive-behavioral therapy for treatment-resistant positive psychotic symptoms; supportive, problem-solving, educationally oriented psychotherapy; family therapy and education programs aimed at helping patients and their families understand the patient's illness, reduce stress, and enhance coping capabilities; social and living skills training; supported employment programs; and/or the provision of supervised residential living arrangements.

Currently accepted treatments for SZ are described in greater detail in the *Practice Guideline for the Treatment of Patients With Schizophrenia American Psychiatric Association*, Second Edition, American Psychiatric Association, 2004, which is incorporated herein by reference in its entirety.

Methods of Determining Treatment Regimens and Methods of Treating SZ, SPD or SD

As described herein, the presence of haplotypes described herein at chromosome 22q13 has been correlated with poor patient prognosis. Thus, the new methods can also include selecting a treatment regimen for a subject determined to be at risk for developing SZ, SPD or SD, based upon the absence or presence of a haplotype associated with SZ as described herein. The determination of a treatment regimen can also be based upon the absence or presence of other risk factors associated with SZ, e.g., as described herein. Therefore, the methods of the invention can include selecting a treatment regimen for a subject having one or more risk factors for SZ, and having a haplotype described herein at chromosome 22q13. The methods can also include administering a treatment regimen to a subject having, or at risk for developing, SZ to thereby treat, prevent or delay further progression of the disease. A treatment regimen can include the administration of antipsychotic medications to a subject identified as at risk of developing SZ before the onset of any psychotic episodes.

As used herein, the term "treat" or "treatment" is defined as the application or administration of a treatment regimen, e.g., a therapeutic agent or modality, to a subject, e.g., a patient. The subject can be a patient having SZ, a symptom of SZ or at risk of developing (i.e., a predisposition toward) SZ. The treatment can be to cure, heal, alleviate, relieve, alter, remedy, ameliorate, palliate, improve or affect SZ, the symptoms of SZ or the predisposition toward SZ.

The methods of the invention, e.g., methods of determining a treatment regimen and methods of treatment or prevention of SZ, can further include the step of monitoring the subject, e.g., for a change (e.g., an increase or decrease) in one or more of the diagnostic criteria for SZ listed herein, or any other parameter related to clinical outcome. The subject can be monitored in one or more of the following periods: prior to beginning of treatment; during the treatment; or after one or more elements of the treatment have been administered. Monitoring can be used to evaluate the need for further treatment with the same or a different therapeutic agent or modality. Generally, a decrease in one or more of the parameters described above is indicative of the improved condition of the subject, although with red blood cell and platelet levels, an increase can be associated with the improved condition of the subject.

The methods can be used, e.g., to evaluate the suitability of, or to choose between alternative treatments, e.g., a particular dosage, mode of delivery, time of delivery, inclusion of adjunctive therapy, e.g., administration in combination with a second agent, or generally to determine the subject's probable drug response genotype. In a preferred embodiment, a treatment for SZ can be evaluated by administering the same treatment or combinations or treatments to a subject having SZ, SPD or SD and a haplotype as described herein at human chromosome 22q13 and to a subject that has SZ but does not have a haplotype as described herein at human chromosome 22q13. The effects of the treatment or combination of treatments on each of these subjects can be used to determine if a treatment or combination of treatments is particularly effective on a sub-group of subjects having SZ, SPD or SD. In other embodiments, various treatments or combinations of treatments can be evaluated by administering two different treatments or combinations of treatments to at least two different subjects having SZ, SPD or SD and a haplotype as described herein in human chromosome 22q13. Such methods can be used to determine if a particular treatment or combination of treatments is more effective than others in treating this subset of SZ, SPD and/or SD patients.

Various treatment regimens are known for treating SZ, e.g., as described herein.

Pharmacogenomics

With regards to both prophylactic and therapeutic methods of treatment of SZ, such treatments may be specifically tailored or modified, based on knowledge obtained from the field of pharmacogenomics. "Pharmacogenomics," as used herein, refers to the application of genomics technologies such as structural chromosomal analysis, to drugs in clinical development and on the market. See, for example, Eichelbaum et al., Clin. Exp. Pharmacol. Physiol. 23:983-985 (1996) and Linder et al., Clin. Chem. 43:254-266 (1997). Specifically, as used herein, the term refers the study of how a patient's genes determine his or her response to a drug (e.g., a patient's "drug response phenotype," or "drug response genotype"). Thus, another aspect of the invention provides methods for tailoring an individual's prophylactic or therapeutic treatment according to that individual's drug response genotype.

Information generated from pharmacogenomic research using a method described herein can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when administering a therapeutic composition, e.g., a cytotoxic agent or combination of cytotoxic agents, to a patient, as a means of treating or preventing SZ.

In one embodiment, a physician or clinician may consider applying knowledge obtained in relevant pharmacogenomics studies, e.g., using a method described herein, when determining whether to administer a pharmaceutical composition, e.g., an antipsychotic agent or a combination of antipsychotic agents, to a subject. In another embodiment, a physician or clinician may consider applying such knowledge when determining the dosage, e.g., amount per treatment or frequency of treatments, of a treatment, e.g., a antipsychotic agent or combination of antipsychotic agents, administered to a patient.

As one example, a physician or clinician may determine (or have determined, e.g., by a laboratory) the haplotype of a subject at chromosome 22q13, and optionally one or more other markers associated with SZ, SPD, or SD, of one or a group of subjects who may be participating in a clinical trial, wherein the subjects have SZ, SPD, or SD, and the clinical trial is designed to test the efficacy of a pharmaceutical composition, e.g., an antipsychotic or combination of antipsychotic agents, and wherein the physician or clinician attempts to correlate the genotypes of the subjects with their response to the pharmaceutical composition.

As another example, information regarding a haplotype associated with an increased risk of SZ, SPD or SD, as described herein, can be used to stratify or select a subject population for a clinical trial. The information can, in some embodiments, be used to stratify individuals that may exhibit a toxic response to a treatment from those that will not. In other cases, the information can be used to separate those that will be non-responders from those who will be responders. The haplotypes described herein can be used in pharmacogenomics-based design and manage the conduct of a clinical trial, e.g., as described in U.S. Pat. Pub. No. 2003/0108938.

Theranostics

Also included herein are compositions and methods for the identification and treatment of subjects who have an increased risk of SZ, SPD or SD, such that a theranostic approach can be taken to test such individuals to determine the effectiveness of a particular therapeutic intervention (e.g., a pharmaceutical or non-pharmaceutical intervention as described herein) and to alter the intervention to 1) reduce the risk of developing adverse outcomes and 2) enhance the effectiveness of the intervention. Thus, in addition to diagnosing or confirming the predisposition to SZ, SPD or SD, the methods and compositions described herein also provide a means of optimizing the treatment of a subject having such a disorder. Provided herein is a theranostic approach to treating and preventing SZ, SPD or SD, by integrating diagnostics and therapeutics to improve the real-time treatment of a subject. Practically, this means creating tests that can identify which patients are most suited to a particular therapy, and providing feedback on how well a drug is working to optimize treatment regimens.

Within the clinical trial setting, a theranostic method or composition of the invention can provide key information to optimize trial design, monitor efficacy, and enhance drug safety. For instance, "trial design" theranostics can be used for patient stratification, determination of patient eligibility (inclusion/exclusion), creation of homogeneous treatment groups, and selection of patient samples that are representative of the general population. Such theranostic tests can therefore provide the means for patient efficacy enrichment, thereby minimizing the number of individuals needed for trial recruitment. "Efficacy" theranostics are useful for monitoring therapy and assessing efficacy criteria. Finally, "safety" theranostics can be used to prevent adverse drug reactions or avoid medication error.

The methods described herein can include retrospective analysis of clinical trial data as well, both at the subject level and for the entire trial, to detect correlations between a haplotype as described herein and any measurable or quantifiable parameter relating to the outcome of the treatment, e.g., efficacy (the results of which may be binary (i.e., yes and no) as well as along a continuum), side-effect profile (e.g., weight gain, metabolic dysfunction, lipid dysfunction, movement disorders, or extrapyramidal symptoms), treatment maintenance and discontinuation rates, return to work status, hospitalizations, suicidality, total healthcare cost, social functioning scales, response to non-pharmacological treatments, and/or dose response curves. The results of these correlations can then be used to influence decision-making, e.g., regarding treatment or therapeutic strategies, provision of services, and/or payment. For example, a correlation between a positive outcome parameter (e.g., high efficacy, low side effect profile, high treatment maintenance/low discontinuation rates, good return to work status, low hospitalizations, low suicidality, low total healthcare cost, high social function scale, favorable response to non-pharmacological treatments, and/or acceptable dose response curves) and a selected haplotype can influence treatment such that the treatment is recommended or selected for a subject having the selected haplotype.

Kits

Also within the scope of the invention are kits comprising a probe that hybridizes with a region of human chromosome at 22q13 and can be used to detect a polymorphism described herein. The kit can include one or more other elements including: instructions for use; and other reagents, e.g., a label, or an agent useful for attaching a label to the probe. Instructions for use can include instructions for diagnostic applications of the probe for assessing risk of SZ in a method described herein. Other instructions can include instructions for attaching a label to the probe, instructions for performing in situ analysis with the probe, and/or instructions for obtaining a sample to be analyzed from a subject. As discussed above, the kit can include a label, e.g., any of the labels described herein. In some embodiments, the kit includes a labeled probe that hybridizes to a region of human chromosome at 22q13, e.g., a labeled probe as described herein.

The kit can also include one or more additional probes that hybridize to the same chromosome, e.g., chromosome 22, or another chromosome or portion thereof that can have an abnormality associated with risk for SZ. For example, the additional probe or probes can be: a probe that hybridizes to human chromosome 22q11-12 or a portion thereof, (e.g., a probe that detects a sequence associated with SZ in this region of chromosome 22), or probes that hybridize to all or a portion of 22q12.3 (e.g., near D22S283), 22q11.2, 22q11.2, 22q11-q13, 1q42.1, 1q42.1, 18p, 15q15, 14q32.3, 13q34, 13q32, 12q24, 1q14-q21, 1q21-q22, 10p15-p13 (e.g., near D10S189), 10q22.3, 8p21, 6q13-q26, 6p22.3, 6p23, 5q11.2-q13.3, and/or 3p25. A kit that includes additional probes can further include labels, e.g., one or more of the same or different labels for the probes. In other embodiments, the additional probe or probes provided with the kit can be a labeled probe or probes. When the kit further includes one or more additional probe or probes, the kit can further provide instructions for the use of the additional probe or probes.

Kits for use in self-testing can also be provided. For example, such test kits can include devices and instructions that a subject can use to obtain a sample, e.g., of buccal cells or blood, without the aid of a health care provider. For example, buccal cells can be obtained using a buccal swab or brush, or using mouthwash.

Kits as provided herein can also include a mailer, e.g., a postage paid envelope or mailing pack, that can be used to return the sample for analysis, e.g., to a laboratory. The kit can include one or more containers for the sample, or the sample can be in a standard blood collection vial. The kit can also include one or more of an informed consent form, a test requisition form, and instructions on how to use the kit in a method described herein. Methods for using such kits are also included herein. One or more of the forms, e.g., the test requisition form, and the container holding the sample, can be coded, e.g., with a bar code, for identifying the subject who provided the sample.

Databases

Also provided herein are databases that include a list of polymorphisms as described herein, and wherein the list is largely or entirely limited to polymorphisms identified as useful in performing genetic diagnosis of or determination of susceptibility to SZ, SPD or SD as described herein. The list is stored, e.g., on a flat file or computer-readable medium. The databases can further include information regarding one or more subjects, e.g., whether a subject is affected or unaffected, clinical information such as endophenotype, age of onset of symptoms, any treatments administered and outcomes (e.g., data relevant to pharmacogenomics, diagnostics or theranostics), and other details, e.g., about the disorder in the subject, or environmental or other genetic factors. The databases can be used to detect correlations between a particular haplotype and the information regarding the subject, e.g., to detect correlations between a haplotype and a particular endophenotype, or treatment response.

Transgenic Animals and Cells

Also provided herein are non-human transgenic animals and cells that harbor one or more polymorphism described herein, e.g., one or more polymorphisms that constitute a haplotype associated with SZ, SPD, or SD. Such animals and cells are useful for studying the effect of a polymorphism on physiological function, and for identifying and/or evaluating potential therapeutic agents for the treatment of SZ, SPD, or SD, e.g., anti-psychotics.

As used herein, a "transgenic animal" is a non-human animal, preferably a mammal in which one or more of the cells of the animal includes a transgene. Examples of transgenic animals include rodents (e.g., rats or mice), non-human primates, rabbits, sheep, dogs, cows, goats, chickens, amphibians, and the like. A transgene as used herein replicates a polymorphism described herein and is integrated into or occurs in the genome of the cells, e.g., the cultured cells or the cells of a transgenic animal. As one example, included herein are cells in which one of the various alleles of the Sult4a1 polymorphism has be re-created, e.g., an allele of D22S1749E. Thus, a transgenic animal or cell can be one in which an endogenous Sult4a1 gene has been altered to include an allele of D22S1749E, e.g., an allele that is associated with an increased risk of SZ, SD, or SPD. Methods are known in the art for generating such animals and cells. e.g., by homologous recombination between the endogenous gene and an exogenous DNA molecule introduced into a cell, e.g., a cell of an animal, e.g., an embryonic cell of an animal, prior to development of the animal.

A transgenic founder animal can be identified based upon the presence of a transgene in its genome. A transgenic founder animal can then be used to breed additional animals carrying the transgene. Moreover, transgenic animals carrying one transgene protein can further be bred to other transgenic animals carrying other transgenes. The invention also includes populations of cells from a transgenic animal as described herein.

Also provided are cells, preferably mammalian cells, e.g., neuronal type cells, in which an endogenous gene has been altered to include a polymorphism as described herein. Techniques such as targeted homologous recombinations, can be used to insert the heterologous DNA as described in, e.g., Chappel, U.S. Pat. No. 5,272,071; WO 91/06667, published in May 16, 1991.

The invention is further illustrated by the following examples, which should not be construed as further limiting. The contents of all references, pending patent applications and published patents, cited throughout this application, are hereby expressly incorporated by reference.

EXAMPLES

Example 1

Analysis of Microsatellite Markers in Chromosome 22

Twenty-seven nuclear families, comprising 212 individuals, each having multiple affected siblings were provided by the Institutes of Mental Health (NIMH) Schizophrenia Genetics Initiative. Self-description of heritage was a follows: African-American, 12 families; European/Mediterranean, 11 families; Hispanic, 2 families; other 2 families. DSM-III criteria were compiled for all subjects by researchers at Columbia University, Harvard University and Washington University. Detailed information on ascertainment, diagnosis and informed consent has been previously provided by these groups (Colinger et al., 1998; Faranoe et al., 1998; Kaufmann et al., Am. J. Genet. 81:282-289 (1998)). Using the DSM-III criteria for SZ, the sample contained 55 affected sibling pairs, and using a broader disease definition that include schizotypal personality disorder and schizoaffective disorder, the sample contained 100 affected sibling pairs.

Initially, linkage was analyzed using a set of 14 microsatellite markers, which are listed in Table 1. As an example, PCR was performed using primers for the microsatellite marker D22s1749e. The upstream primer sequence was 5'-CAGCCGCACGCCATGGAACTCGAAG-3' (SEQ ID NO:1) and the downstream primer sequence was 5'-GGCGC-CATGACGTCACGCCTGC-3' (SEQ ID NO:2). Each 10 µl reaction contained a final concentration of 5 ng of genomic DNA, 10× buffer (Roche), 0.16 U of AmpliTaq Gold, 2.0 mM $MgCl_2$, 1 mM of each dNTP, 0.33 µM of forward and reverse primers, and 10% DMSO. PCR conditions consisted of an initial enzyme activation at 95° C. for 5 min, followed by 35 cycles of 93° C. for 2 min, 92° C. for 1 min, 71° C. for 30 s, and 72° C. for 2 min, and a final incubation at 72° C. for 5 min. PCR products were analyzed and fragment size was determined using the Biomek CEQ 8000 Analysis System.

TABLE 1

Markers on Human Chromosome 22q

| Marker[a] | Kosambi cM[b] | Distance Mb[b,c] |
|---|---|---|
| D22s311 | | |
| D22s446 | 2.6000 | 20.3437-20.3439 |
| D22s315 | 11.5000 | 24.3404-24.3406 |
| D22s275 | 22.8000 | |
| D22s683 | 30.2000 | 34.8384-34.8389 |
| D22s270 | 41.5000 | 41.3780-41.3782 |

TABLE 1-continued

Markers on Human Chromosome 22q

| Marker[a] | Kosambi cM[b] | Distance Mb[b,c] |
|---|---|---|
| rs138060 | 44.4000 | 42.5477 |
| rs138097 | 44.4678 | 42.5755 |
| D22s1749e | 44.4863 | 42.5831-42.5833 |
| rs138110 | 44.4897 | 42.5847 |
| D22s274 | 47.0187 | 43.5897-43.5899 |
| D22s1149 | 51.3187 | 44.9934-44.9935 |
| D22s1170 | 56.7187 | 46.6712-46.6714 |
| rs738596 | 59.4417 | 47.6932 |
| rs738598 | 59.4857 | 47.7102 |
| D22s1169 | 59.5187 | 47.7230-47.7231 |
| rs2073224 | 59.6587 | 47.7490 |
| rs738615 | 59.6617 | 47.7495 |
| rs135221 | 60.1217 | 47.8325 |
| rs767219 | 60.8517 | 47.9633 |
| sJCW16 | 60.8917 | 47.9709 |
| rs848768 | 61.7811 | 48.0389 |
| rs848728 | 62.0582 | 48.0616 |
| rs2269523 | 62.3402 | 48.0898 |
| rs737734 | 62.4936 | 48.1051 |
| rs136770 | 62.6528 | 48.1211 |
| D22s526 | 63.0417 | 48.1599-48.1602 |
| rs134474 | 63.7602 | 48.2321 |
| rs134472 | 63.7671 | 48.2328 |
| rs134454 | 63.8946 | 48.2455 |
| rs135819 | 64.2029 | 48.2763 |
| rs763126 | 64.2360 | 48.3094 |
| rs916363 | 64.2650 | 48.3384 |
| rs1573726 | 64.2803 | 48.3537 |
| rs138817 | 64.3833 | 48.4839 |
| rs138844 | 64.4047 | 48.5053 |
| rs137853 | 64.6264 | 48.7459 |
| rs1053744 | 65.0191 | 49.1759 |
| D22s1744 | 65.1608 | 49.3178 |
| D22s1743 | 65.3608 | 49.3418 |

[a]Markers are listed from 22 cen to 22 qter
[b]Brennan et al. Genomics 63, 430-423 (2000)
[c]Ensembl Simple parametric models did not give significant evidence for linkage, regardless of the mode of inheritance or the degree of penetrance assumed. However, a model assuming genetic heterogeneity resulted in maximum LOD score of 2.6 at marker D22s270 (θ=0) for SZ and a value of 3.6 for a broader definition of disease that included schizotypal personality disorder (SPD; FIG. 1). In agreement with the findings of others, some evidence for linkage near marker D22s683 was seen using the narrow definition (Vallada et al., Psychiatr. Genet. 5:127-30 (1995); DeLisi et al., Am. J. Psychiatry 159:803-12 (2002); Takahashi et al., Am. J. Med. Genet. 120B:11-7 (2003)). Similar peaks at D22s270 resulted from nonparametric linkage analysis giving LOD scores of 2.5 and 2.7, for the narrow and broad disease definitions, respectively (FIG. 1). Note that the broader disease definition results both in higher LOD scores for D22s270 and an increase in the smaller, more distal peak centered at sJCW16.

Initial mapping of D22s1749e was performed using the MultiMap program (version 2.40) as described previously (Cox Matise et al., Nature Genetics 6:384-390 (1994); Cox-Matise et al., Multimap, Automated genetic linkage mapping, version 2.4. (1996); Brennan et al., Genomics 63:430-432 (2000)). TDT analysis was performed using TRANSMIT (version 2.5.2) (Clayton, Am. J. Hum. Genet. 65(4):1170-7 (1999)), with rare haplotypes aggregated so as to prevent elevation of $X^2$ values that can arise due to expectations for rare haplotypes. The resulting global P values for the $X^2$ analyses estimate the significance of the transmission distribution for all haplotypes combined, with rare haplotypes being treated as a single haplotype. Similarly, $X^2$ values for transmission of individual genotypes and haplotypes, with one degree of freedom, are determined by TRANSMIT.

Example 2

Identification of Sult4a1 as a Candidate Gene

A search for candidate genes near marker D22s270, performed using public database resources, identified the sulfotransferase-4A1 gene (Sult4a1), which is located within 1.2 Mb of this microsatellite marker, and encodes a brain-specific sulfotransferase believed to be involved in dopamine catabolism (Falany et al., Biochem J. 346:857-64 (2000); Sakakibara et al., Gene 285:39-47 (2002); Liyou et al., J. Histochem. Cytochem. 51:655-64 (2003)).

Alignment of the genomic sequences with several corresponding cDNA sequences (Z97055, AF176342, AF188698, AF251263, AK091700, A1832543) indicated, in all likelihood, that the DNA encoding the 5' non-translated leader region of the Sult4a1 mRNA was polymorphic, having a varying number of imperfect GCC repeats (primary accession numbers Z97055, AF176342, AF188698, AF251263, AK091700, A1832543). To evaluate this possibility, a PCR procedure was developed to amplify the genomic region at the 5' end of the gene.

Briefly, SNPs were analyzed using Applied Biosystems Assays-on-Demand SNP kits. Each 5 μl reaction contained 2.5 μl of Taq Man polymerase, 0.25 μl of 20×SNP assay and 2.25 μl of 10 ng genomic DNA. PCR conditions consisted of an initial enzyme activiation at 95° C. for 10 min, followed by 40 cycles of 95° C. for 15 sec, and 60° C. for 1 min. PCR products were analyzed using the ABI Prism 7900HT Sequence Detection System. The region is very G-C rich and refractory to amplification. Nonetheless, reproducible amplification of the region was obtained for all families, confirming Mendelian inheritance in all cases.

In this sample of families, seven alleles, with one two five nucleotides separating adjacent alleles in the series, were observed. The MultiMap program was used to confirm that D22s1749e mapped approximately 10 cM distal to D22s683. Table 2 lists the location, in mb, of this new microsatellite marker and the three nearby SNPs that were used for TDT analysis.

TABLE 2

Markers Used

| Marker | Location on Chromosome 22 (Mb[a]) |
|---|---|
| rs138060 | 42.5477 |
| rs138097 | 42.5755 |
| D22s1749e | 42.5831 |
| rs138110 | 42.5847 |

[a]NCBI: .ncbi.nlm.nih.gov/SNP/

In this sample of families, seven alleles of marker D22s1749e ranging in size from 198 to 216 nuleotides were observed. (Table 3).

TABLE 3

Observed Alleles of D22s1749e

| Size (nt) | Observed frequency[a] |
|---|---|
| 198 | 0.0022 |
| 202 | 0.0088 |
| 207 | 0.385 |

TABLE 3-continued

Observed Alleles of D22s1749e

| Size (nt) | Observed frequency[a] |
|---|---|
| 209 | 0.033 |
| 212 | 0.286 |
| 213 | 0.165 |
| 216 | 0.022 |

[a]Frequency for the NIMH sample using only those parental genotypes that were directly observed or that could be unambiguously inferred.

Figure 2:
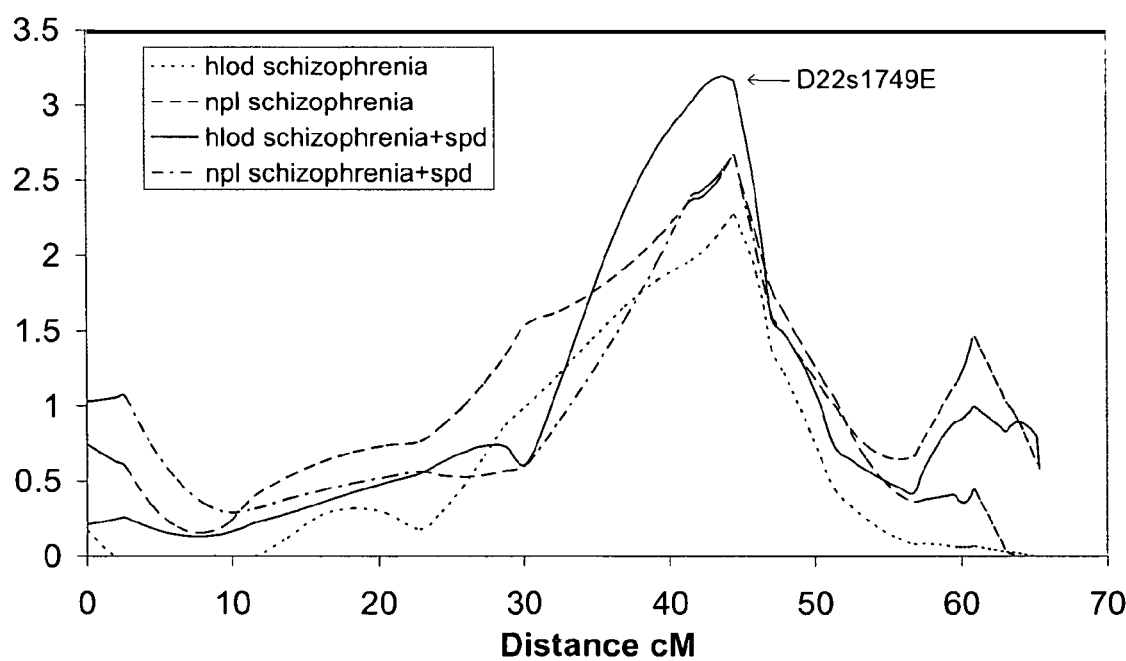
FIG. 2 is a line graph illustrating LOD scores for markers at the indicated locations on the long arm of chromosome 22, including the new marker D22S1749E, the location of which is indicated.

Including this new is new marker in the linkage analysis did not alter the location of the maximum LOD scores, which were still observed at marker D22S270. Owing to the increased information content, the maximum LOD values increased somewhat. Assuming heterogeneity, a maximum LOD score of 2.90 was obtained using DSM IIIR criteria, and a maximum LOD score of 3.96 was obtained for a broader disease definition that included schizotypal personality disorder (FIG. 2). Again, nonparametric linkage analysis provided suggestive evidence for linkage at the same location, with LOD scores of 2.6 and 2.8 for the narrow broad definitions, respectively (FIG. 1, solid and broken black lines).

The sample was further expanded by adding 17 more families to the original 27 families. Using the D22s1749e marker in linkage analysis for the pooled sample (using a dominant model assuming genetic heterogeneity, a penetrance of 50% for a heterozyote and a 1% allele) a single point heterogeneous LOD score of 4.78 was obtained for the combined sample of 44 families ($\alpha$=0.7).

Consistent with the initial findings, for the pooled sample, D22S1749E showed significant deviation from expectation for transmission to affected offspring using TRANSMIT (Clayton Am J Hum Genet. 65(4):1170-7 (1999) (P=0.015 for SZ, and P=0.006 for the broader definition including SPD).

Example 3

Identification of Haplotypes Including Markers in Sult4a1

The Sult4a1 candidate gene was further evaluated by Transmission/Disequilibrium Test (TDT) analysis employing the new microsatellite marker, along with three SNPs in the gene. Table 4 summarizes the results of the TDT analysis for these polymorphisms and haplotypes involving them. Significant results were seen for D22s1749e and various haplotypes involving D22s1749e and the three SNPs in Sult4a1. In most cases, the results were more significant for a narrow definition of schizophrenia (SZ), than for broader definitions that included schizotypal personality disorder (SPD) or schizoaffective disorder (SD).

TABLE 4

TDT Analysis of Sult4a1 Markers

| | | P Value for Disease Definition[a] | | |
|---|---|---|---|---|
| Marker(s) | df | SZ | SZ + SPD | SZ + SPD + SD |
| D22s1749e | 4[b] | 0.04 | 0.05 | 0.04 |
| rs138060-rs138097 | 3[b] | 0.04 | 0.12 | 0.12 |
| rs138060-D22s1749e | 7[b] | 0.008 | 0.004 | 0.17 |
| rs138060-rs138097-D22s1749e | 9[c] | 0.0014 | 0.0006 | 0.0055 |
| rs138060-D22s1749e-rs138110 | 10[c] | 0.0095 | 0.0017 | 0.018 |
| rs138097-D22s1749e-rs138110 | 7[c] | 0.04 | 0.03 | 0.05 |
| rs138060-rs138097-D22s1749e-rs138110 | 11[c] | 0.014 | 0.0064 | 0.04 |

[a]SZ = schizophrenia, SPD = schizophrenia + schizotypal personality disorder, SD = schizoaffective disorder.
[b]Global chi square values as determined by Transmit, with haplotypes having a frequencies of 3% or less aggregated.
[c]Global chi square values as determined by Transmit with haplotypes having a frequencies of 14% or less aggregated.

Example 4

Identification of Microsatellite Markers in 22q13 Showing TD

All of the microsatellite polymorphisms listed in Table 1 were tested for evidence of transmission disequilibrium. Other than D22s1749e, only D22s256 showed significant results (Table 5).

D22s256 was evaluated using PCR with the following conditions: 95° C., 12 min, 1 cycle; 94° C., 15 sec, 60° C., 15 sec, 72° C., 30 sec, 10 cycles; 89° C., 15 sec, 60° C., 15 sec, 72° C., 30 sec, 25 cycles; 72° C., 30 min, 1 cycle. The primers were: Left: 5'-AGAGCAAGACTCTGTCTCAACA-3' (SEQ ID NO:3); Right, 5'-TTCTCCTTCACTTTCTGCCATG-3' (SEQ ID NO:4s). The left primer has a HEX florescent label at the 5' end. PCR products were analyzed using an ABI PRISM 377 DNA Sequencer with GeneScan and Genotyper software packages. The expected product size was 250 to 308 nt.

In this sample of families, 16 of the 23 alleles of D22s256, ranging in size from 258 to 305 nt, were observed. Using the narrow DSM-1II criteria for SZ provided significant results for this marker (P=0.003). Broader disease definitions including SPD or both SPD and schizoaffective disorder (SD) provided even more striking results (P=0.002 and P=0.00009, respectively).

TABLE 5

TDT Analysis of Marker D22s526

| Disease definition | Chi Square[a] | P[b] |
|---|---|---|
| SZ | 24.97 | 0.003 |
| SZ + SPD | 31.93 | 0.0002 |
| SZ + SPD + SD | 33.95 | 0.00009 |

[a]Global chi square values as determined by Transmit, with haplotypes having a frequencies of 3% or less aggregated.
[b]Probability with 9 df.

Example 5

Identification of Haplotypes Associated with SZ, SPD, and SD-2 and 3 Marker Haplotypes Tables 6 and 7 list two and three marker haplotypes, respectively, that showed highly significant deviations from expected transmission frequencies for affected offspring under the broadest disease definition, including SZ, schizoaffective disorder, and schizotypal personality disorder. The distances are taken from the NCBI database (SNPdb build 125; Genome Build 35.1, September, 2005).

TABLE 6

TDT: Two marker haplotype p ≤ 0.001 SZ + SD + SPD

| Marker | p value | Distances Mb |
|---|---|---|
| rs2073224-D22s526 | 1.5217E−05 | 47.7490- 48.1602 |
| rs738615-D22s526 | 1.5217E−05 | 47.7495- 48.1602 |
| rs767219-D22s526 | 0.0010 | 47.9633- 48.1602 |
| rs767219-rs1573726 | 0.0002 | 47.9633- 48.3537 |
| D22s526-rs134472 | 0.0003 | 48.1602- 48.2328 |
| D22s526-rs763126 | 3.787E−07 | 48.1602- 48.3094 |
| D22s526-rs1573726 | 0.0004 | 48.1602- 48.3537 |
| D22s526-rs138817 | 8.741E−09 | 48.1602- 48.4839 |
| D22s526-rs138844 | 7.976E−10 | 48.1602- 48.5053 |

TABLE 7

TDT: Three marker haplotype p ≤ 0.001 SZ + SD + SPD

| Markers | p value | Distances Mb |
|---|---|---|
| rs2073224-rs135221-rs767219 | 7.4504E−06 | 47.7490- 47.9633 |
| rs2073224-rs135221-rs138817 | 4.0105E−09 | 47.7490- 48.4839 |
| rs2073224-rs767219-rs737734 | 8.3037E−29 | 47.7490- 48.1051 |
| rs2073224-rs767219-rs1573726 | 4.26677E−05 | 47.7490- 48.3537 |
| rs2073224-rs2269523-rs134472 | 1.9771E−09 | 47.7490- 48.2328 |
| rs135221-rs767219-rs916363 | 9.7080E−15 | 47.8325- 48.3384 |

TABLE 7-continued

TDT: Three marker haplotype p ≤ 0.001 SZ + SD + SPD

| Markers | p value | Distances Mb |
|---|---|---|
| rs135221-rs767219-rs1573726 | 0.0002 | 47.8325- 48.3537 |
| rs135221-rs848768-rs1573726 | 4.7207E−05 | 47.8325- 48.3537 |
| rs135221-rs848768-rs138817 | 6.6501E−08 | 47.8325- 48.4839 |
| rs135221-rs848768-rs1053744 | 1.1167E−08 | 47.8325- 49.1759 |
| rs135221-rs737734-rs134472 | 9.8432E−06 | 47.8325- 48.2328 |
| rs135221-rs134474-rs1053744 | 1.6512E−12 | 47.8325- 49.1759 |
| rs135221-rs916363-rs138817 | 8.9512E−242 | 47.8325- 48.4839 |
| rs135221-rs916363-rs1053744 | 2.2041E−05 | 47.8325- 49.1759 |
| rs767219-rs848768-rs2269523 | 0.0001 | 47.9633- 48.0898 |
| rs767219-rs848768-rs737734 | 9.9720E−06 | 47.9633- 48.1051 |
| rs767219-rs848768-rs1573726 | 5.1963E−05 | 47.9633- 48.3537 |
| rs767219-rs848768-rs138817 | 2.5709E−08 | 47.9633- 48.4839 |
| rs767219-rs848728-rs737734 | 0.0009 | 47.9633- 48.1051 |
| rs767219-rs848728-rs136770 | 1.4604E−10 | 47.9633- 48.1211 |
| rs767219-rs848728-rs134472 | 9.8306E−23 | 47.9633- 48.2328 |
| rs767219-rs848728-rs1573726 | 0.0006 | 47.9633- 48.3537 |
| rs767219-rs2269523-rs737734 | 4.0063E−16 | 47.9633- 48.1051 |
| rs767219-rs2269523-rs1573726 | 0.0004 | 47.9633- 48.3537 |
| rs767219-rs737734-rs916363 | 3.8423E−06 | 47.9633- 48.3384 |
| rs848768-rs2269523-rs138817 | 3.3795E−08 | 48.0389- 48.4839 |
| rs136770-rs134474-rs763126 | 3.4059E−05 | 48.1211- 48.3094 |

Additional haplotypes within this region were also evaluated, and the results are presented in Table 8. Haplotypes listed in bold show highly significant results for the narrowest disease definition of SZ.

TABLE 8

Examples of additional haplotypes p ≤ 0.001 for various disease definitions[a]

| | Disease definition | | | |
|---|---|---|---|---|
| Single Nucleotide Haplotypes | SZ[b] | SZ + SD[c] | SZ + SPD[d] | SZ + SD + SPD[e] |
| rs1355221-rs1053744 | 0.1309 | 0.0648 | 0.0003 | 3.96E−05 |
| rs738596-rs763126 | 0.082 | 0.1049 | 0.4214 | 1.60E−16 |
| rs135221-rs48768-rs1053744 | 0.0717 | 0.6809 | 0.0018 | 3.26E−27 |
| rs135221-rs738615-rs138817 | 0.0677 | 0.8333 | 0.3203 | 5.47E−11 |
| rs136770-rs134474-rs763126 | 0.0635 | 0.0792 | 2.28E−05 | 3.4E−05 |
| rs135221-rs738598-rs2269523 | 0.0476 | 0.0021 | 0.0233 | 0.0011 |
| rs135221-rs916363-rs138817 | 0.0320 | 0.0002 | 0.0214 | 2.2E−05 |
| rs135221-rs763126-rs1573726 | 0.0154 | 0.0005 | 0.0162 | 0.0017 |
| rs848768-rs738598-rs1573726 | 0.0065 | 0.0031 | 0.0109 | 1.48E−26 |
| rs738598-rs2269523-rs1573726 | 0.0059 | 0.0015 | 0.0109 | 7.51E−17 |
| rs738598-rs738615-rs1573726 | 0.0041 | 0.0010 | 0.5106 | 0.6582 |
| rs737734-rs136770-rs763126 | 0.0010 | 0.0002 | 0.0241 | 0.0126 |
| rs738598-rs1573726-rs138844 | 0.0008 | 0.0002 | 0.0003 | 7.18E−05 |
| rs738596-rs738598-rs1573726 | 0.0007 | 0.0003 | 0.0031 | 0.0023 |
| rs738596-rs1573726 | 0.0004 | 0.0007 | 0.0024 | 0.0040 |
| rs738598-rs1573726 | 0.0004 | 0.0002 | 0.0109 | 0.0058 |
| rs135819-rs1573726 | 0.0004 | 0.0008 | 0.0448 | 0.0467 |
| rs738598-rs138844-rs1053744 | 0.0002 | 2.39E−05 | 0.0043 | 0.0012 |
| rs1573726 | 8.06E−05 | 0.0001 | 0.0013 | 0.0015 |
| rs153221-rs763126 | 4.28E−05 | 0.0073 | 0.0021 | 0.0310 |
| rs135221-rs2269523-rs737734 | 9.76E−06 | 0.1564 | 0.0001 | 0.0560 |
| rs737734-rs134474-rs134454 | 5.76E−07 | 3.85E−05 | 0.7276 | 0.5819 |
| rs135221-rs848768-rs763126 | 3.80E−11 | 0.0273 | 0.0951 | 0.1246 |
| rs2073224-rs763126-rs138844 | 4.10E−53 | 0.0023 | 0.0061 | 0.0071 |
| rs738615-rs763126-rs138844 | 4.10E−53 | 0.0023 | 0.0061 | 0.0071 |

[a]As determined by TRANSMIT (rare haplotypes pooled)
[b]SZ = schizophrenia
[c]SZ + SD = schizophrenia + schizoaffective disorder
[d]SZ + SPD = schizophrenia + schizotypal personality disorder
[e]SZ + SD + SPD = schizophrenia + schizoaffective disorder + schizotypal personality disorder Example 6

Identification of Haplotypes Associated with SZ—Alleles of Sult4A

Table 9 summarizes $X^2$ tests for specific haplotypes that were determined to be transferred more frequently or less frequently than expected to affected offspring using the narrow DSM-III definition of SZ. The 213 nt allele for D22s1749e was transmitted more often than expected, and the 207 nt allele less often than expected to affected offspring. None of the SNPs, when used alone, showed $X^2$ values for transmission disequilibrium that were significant at the P<0.01 level. However, several haplotypes involving these SNPs in combination with D22s1749e showed significant transmission distortion (Table 9).

TABLE 9

TDT Analysis for Specific Haplotypes (P < 0.01)

| Marker(s)[a] | Haplotype[b] | Transmission to Affected Offspring (DSM-III schizophrenia) | | |
|---|---|---|---|---|
| | | Higher/Lower than expected | $\chi^2$ (1 df) | P |
| D22s1749e | 213 | higher | 7.23 | 0.0071 |
| rs138060-D22s1749e | A-213 | higher | 7.89 | 0.0049 |
| rs138060-D22s1749e | C-207 | lower | 7.58 | 0.0059 |
| rs138060-rs138097-D22s1749e | C-T-207 | lower | 6.73 | 0.0094 |
| rs138060-rs138097-D22s1749e | A-T-213 | higher | 8.02 | 0.0046 |
| rs138060-D22s1749e-rs138110 | A-213-G | higher | 7.66 | 0.0056 |
| rs138097-D22s1749e-rs138110 | T-213-G | higher | 8.01 | 0.0046 |
| rs138060-rs138097-D22s1749e-rs138110 | A-T-213-G | higher | 7.83 | 0.0051 |

[a]Polymorphisms are listed in proximal to distal order on the chromosome.
[b]Genotypes give the length (nt) for D22s1749e and specific nucleotide descriptions for each SNP, listed in the same order as the marker names.

The 213 nt allele of Sult4a1 appears to be transmitted more often than expected to affected children. The 216 nt allele occurred too rarely in this small sample for the TDT analysis to be statistically valid, but tentatively, it too appears to be preferentially transmitted to affected offspring. These alleles are predicted to encode an mRNA with a longer 5' nontranslated leader sequence than the shorter alleles. As one theory, not meant to be binding, the longer 5' leader sequences might lower translatability of the mRNAs and result in lower final levels of the Sult4a1 enzyme. At present, the major physiological substrate(s) of the Sult4a1 isozyme is unknown, but in vitro, it functions on a variety of phenolic compounds structurally resembling the catecholamines (Sakakibara et al., Gene 285:39-47 (2002)).

These findings add to a body of results pointing to a role for chromosome 22q in the etiology of SZ. In agreement with the findings of others (Vallada et al., Psychiatr. Genet. 5:127-30 (1995); DeLisi et al., Am J Psychiatry 159:803-12 (2002); Takahashi et al., Am. J. Med. Genet. 120B:11-7 (2003)), evidence for linkage near marker D22s683 is seen at about 30 cM on the linkage map, but the highest LOD score was obtained at 41.5 cM corresponding to marker D22s270. The smaller peak at D22s683 was most prominent with the narrow disease definition, while a broader disease definition results in an additional distal linkage peak centered at sJCW16.

Based on TDT analysis, both the Sult4a1 candidate gene and the more distal region of 22q appear to contribute to the genetic predisposition to SZ. In this sample of families, TDT provided suggestive evidence for a role of the Sult4a1 candidate gene located near marker D22s270, representing the major LOD score peak observed in linkage analysis. In contrast, no evidence of transmission disequilibrium was seen for most microsatellite markers, including D22s683 and D22s270. However, highly significant results, particularly for broader disease definitions, were seen for marker D22s526, which is located within 200 kb of marker sJCW16, corresponding to the more distal peak we see in linkage analysis.

Taken together, these results support a two locus model, involving a proximal locus, perhaps most significant for a narrowly defined SZ and a more distal locus near D22s526, most likely contributing additionally to SPD, SD and other SZ-spectrum disorders. It now seems clear that sequences within these chromosomal segments contribute to the genetic predisposition to these disorders.

Example 7

Identification of Haplotypes Associated with SZ—Microdeletions at D22s526

As described above, numerous two and three SNP haplotypes spanning the distal region show highly significant distortions in transmission ratios for DSM-IIIR diagnosed SZ and broader disease definitions ($P<10^{-5}$). A close evaluation of the haplotypes revealed particular SNP haplotypes that are preferentially transmitted. In about half of the NIMH families, these SNP haplotypes occur as part of a larger haplotype involving a small subset (two to four per population) of the 23 alleles of a highly polymorphic marker (D22s526).

The D22s526 microsatellite marker was evaluated in 561 unrelated individuals from the Louisville Twin Family Study (comprising approximately 70% EA, 25% AA and 5% other). As described in Brennan et al., Genomics 63(3):430-2 (2000), a total of 23 alleles of D22s526 were observed, ranging in size from 254 nt to 308 nt inclusive. These alleles are numbered from 1 to 23 (smallest to largest) in Table 10.

TABLE 10

Analysis of D22s526 in Control Sample and NIMH Schizophrenia Families

| Allele | Allele frequency in controls[a] | Expected frequency of homozygotes[b] | Observed frequency of apparent homozygotes in controls (N = 561) | Occurrences of allele in NIMH sample[c] (N = 52) [observed frequency] | Observed frequency of apparent homozygotes in NIMH sample[d] (N = 26) |
|---|---|---|---|---|---|
| 1 | 0.007 | <0.1% | 0 | 0 | 0 |
| 2 | 0.005 | <0.1% | 0 | 0 | 0 |

TABLE 10-continued

Analysis of D22s526 in Control Sample and NIMH Schizophrenia Families

| Allele | Allele frequency in controls[a] | Expected frequency of homozygotes[b] | Observed frequency of apparent homozygotes in controls (N = 561) | Occurrences of allele in NIMH sample[c] (N = 52) [observed frequency] | Observed frequency of apparent homozygotes in NIMH sample[d] (N = 26) |
|---|---|---|---|---|---|
| 3 | 0.065 | 0.4% | 0 | 2 [0.038] | 0 |
| 4 | 0.102 | 1% | 0.4% | 3 [0.058] | 0 |
| 5 | 0.041 | 0.2% | 0 | 0 | 0 |
| 6 | 0.112 | 1.3% | 0.4% | 1 [0.019] | 0 |
| 7 | 0.041 | 0.2% | 0 | 2 [0.038] | 0 |
| 8 | 0.107 | 1.1% | 0 | 6 [0.115] | 0 |
| 9 | 0.033 | 0.1% | 0.2% | 2 [0.038] | 3.8% |
| 10 | 0.149 | 2.2% | 0.7% | 9 [0.173] | 7.7% |
| 11 | 0.033 | 0.1% | 0.2% | 1 [0.019] | 0 |
| 12 | 0.102 | 1.0% | 0.2% | 9 [0.173] | 7.7% |
| 13 | 0.080 | 0.6% | 0.7% | 1 [0.019] | 0 |
| 14 | 0.051 | 0.2% | 0 | 6 [0.115] | 3.8% |
| 15 | 0.074 | 0.5% | 0.5% | 0 | 0 |
| 16 | 0.020 | <0.1% | 0.2% | 0 | 0 |
| 17 | 0.063 | 0.4% | 0.2% | 6 [0.115] | 11.5% |
| 18 | 0.003 | <0.1% | 0 | 1 [0.019] | 0 |
| 19 | 0.038 | 0.1% | 0.2% | 1 [0.019] | 0 |
| 20 | 0.002 | <0.1% | 0 | 0 | 0 |
| 21 | 0.018 | <0.1% | 0 | 1 [0.019] | 0 |
| 22 | 0.009 | <0.1% | 0 | 1 [0.019] | 0 |
| 23 | 0.054 | 0.3% | 0.2% | 0 | 0 |

[a]Frequency observed in 561 unrelated individuals representing a cross section of the population in the Louisville metropolitan area. The values do not add to 1.00 due to rounding.
[b]Expected frequency of homozygous individuals for an unselected sample given Hardy-Weinberg assumptions.
[c]Occurrences and empirical frequencies of the alleles in 26 probands from NIHM Schizophrenia Genetics Initiative.
[d]Observed frequency of apparently homozygous (or hemizygous) individuals in a sample of 26 probands from NIHM Schizophrenia Genetics Initiative.

An apparent heterozygosity of 97.5% was found in the unselected sample of 561 unrelated individuals. In other words, one expects only about 2.5% of randomly sampled individuals to be homozygous for this marker. By contrast, 9 of 27 (33%) of the NIMH probands (i.e., the individuals first identified as affected for each particular family) are apparent homozygotes (5 of 13 EA; 2 of 12 AA; 1 of 2 "other"; Fisher Exact Test P=2×10$^{-5}$; OR 15.3; Log odds=2.7).

At least a portion of the apparent homozygosity for this region appears to be due to microdeletions segregating in some families. Mendelian inheritance patterns for the control sample showed that 4 of the 15 apparently homozygous individuals could be hemizygous, because they fail to transmit the expected allele to one or more children. Thus, perhaps about 0.5% of individuals from the unselected population are hemizygous for D22s526.

A closer look at the NIMH families indicates that microdeletions are likely. Six of the eight probands with apparent homozygosity for the microsatellite polymorphism also have an adjacent region of presumptive hemizygosity extending over approximately 200 to 300 kb in one or both directions. Furthermore, in AA families in particular, there are five additional probands who appear to carry deletions that do not uncover the microsatellite but do uncover nearby extended regions of at least 100 to 500 kb, as judged by apparent homozygosity for certain (and various) infrequent haplotypes.

DNA from one or both parents and multiple siblings can be used to rule out most trivial explanations for these results. Loss of homozygosity during immortalization and propagation of cell lines is unlikely, as the same presumptive deletion is carried by multiple family members. Consanguinity and resulting extended regions of homozygosity cannot explain the results either, because other polymorphic markers, even on the same chromosome, do show extensive homozygosity.

These novel microdeletions may confer significant risk of developing schizophrenia spectrum disorders (SZ, SD, and/or SPD). As one theory, not meant to be limiting, using the 22q11 deletion syndrome as a prototype, is that the microdeletions either uncover one or more specific "risk" alleles, or that haploinsufficiency per se confers increased risk.

Example 8

Exemplary Markers Within 1 Linkage Disequilibrium Unit (1 LDU)

On-line public resources (HapMap.org) were used to identify exemplary SNPs that are in linkage disequilibrium with some of the SNPs described herein, as follows:

rs738596

SNPs within 1 LDU of marker rs738596 in African American populations include: rs5770635, rs17000207; in European American Populations include: rs4823940, rs13053183, rs4824067, rs9628096; in Chinese populations include: rs5770579, rs8136613, rs4824067, rs17824774, rs5770632, rs9628096, rs5770634, rs5770635, rs9628100; and in Japanese populations include: rs2024698, rs9616622, rs5770581, rs4824067.

rs2073224

SNPs within 1 LDU of marker rs2073224 in African American populations include: rs9616222, rs5769820, rs5769821, rs17178537, rs4823974, rs2064542; in European American populations include: rs9616222, rs5769820, rs5769821, rs17178537, rs6009133, rs6009134, rs4823974, rs2064542.

rs738615

SNPs within 1 LDU of marker rs738615 in Chinese populations include: rs4823908, rs2073225, rs761666, rs2064542; and in Japanese populations include: rs9616409, rs4823908, rs2073225, rs761666, rs2064542.

rs848768

SNPs within 1 LDU of marker rs848768 in African American populations include: rs12165304, rs9627698, rs9616561, rs9627966, rs12169496, rs12628115, rs11090946, rs848751, rs848750; in European American Populations include: rs2319174, rs739049, rs7287432, rs9616561, rs848764, rs848750; in Chinese populations include: rs739049, rs848764, rs12628115, rs11090946, rs848751, rs848750; and in Japanese populations include: rs8135938, rs848751, rs848752.

rs737734

SNPs within 1 LDU of marker rs737734 in European American populations include: rs5769607, rs5770363, rs714007, rs713997, rs5770369, rs7285315, rs2873922, rs2097363, rs7510746; and in Chinese populations include: rs5769607, rs8140231, rs713919, rs2097363, rs4824032, rs2187751.

rs134474

SNPs within 1 LDU of marker rs134474 in African American populations include: rs6520121, rs17001084, rs17001087, rs3810643; in European American Populations include: rs9616663, rs2873932, rs470019, rs470018, rs470017, rs134459, rs134458, rs134456.

rs763126

SNPs within 1 LDU of marker rs763126 in African American populations include: rs135786, rs135787, rs135788, rs135789, rs135791, rs763124, rs135800, rs135804, rs8140984, rs135821, rs135827, rs135832, rs2319345, rs135833, rs135846, rs6009767, rs5769691, rs2071894, rs5770562, rs2071893, rs135854, rs135855, rs17001439, rs5770567, rs2007024, rs17182154, rs17001168, rs2187891, rs9616687, rs17001172, rs739247, rs2071890; in European American populations include: rs9616685, rs5769691, rs2071894, rs135853, rs5770562, rs2071893, rs135854, rs135855, rs5770567, rs2007024, rs739247, rs135861, rs2071890, rs12628438, rs10854876, rs6009782, rs135875, rs135876, rs135877; in Chinese populations include: rs763124, rs135845, rs135846, rs135853, rs135827, rs135854, rs135855; rs2319345, rs9616685, rs5769691, rs2071894, rs5770562, rs135854, rs135855, rs5770567; and in Japanese populations include: rs135819, rs135827, rs135831, rs470058, rs2319345, rs135846, rs1008320, rs5769691, rs2071894, rs135853, rs2071893, rs2071892, rs135854, rs135855, rs135856, rs10854874.

rs138844

SNPs within 1 LDU of marker rs138844 in African American populations include: rs138841, rs139818, rs10483250; in European American populations include: rs139818, rs138840, rs138841; in Chinese populations include: rs6009860, rs10483250, rs138841; and in Japanese populations include: rs10483250, rs6009870, rs5770689, rs138816, rs138820, rs138821, rs138823, rs138827, rs6009874, rs138840, rs138841, rs138843.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of determining a human subject's risk of developing schizophrenia (SZ), the method comprising detecting the presence of a haplotype in a sample from the subject, wherein the haplotype comprises:
   (i) an A allele at rs138060;
   (ii) a C allele at rs138097; and
   (iii) a G allele at rs138110,
   wherein the presence of the haplotype indicates that the subject has an increased risk of developing the disorder.

2. The method of claim 1, wherein the haplotype further comprises an allele at microsatellite marker D22s1749e comprising more than 207 nucleotides.

3. The method of claim 1, wherein detecting the presence of a haplotype comprises:
   obtaining a sample comprising DNA from the subject; and
   determining the identity, presence or absence of the polymorphisms in the sample.

4. The method of claim 1, wherein detecting the presence of a haplotype comprises reviewing a subject's medical history, wherein the medical history includes information regarding the polymorphisms.

5. The method of claim 3, wherein the sample is obtained from the subject by a health care provider.

6. The method of claim 3, wherein the sample is provided by the subject without the assistance of a health care provider.

7. The method of claim 1, further comprising determining the presence or absence of one or more additional markers associated with schizophrenia.

8. The method of claim 1, wherein the subject is a patient having, or at risk of, schizophrenia.

9. The method of claim 1, wherein the subject is suffering from early, intermediate or aggressive schizophrenia.

10. The method of claim 1, wherein the subject has one or more risk factors associated with SZ.

11. The method of claim 10, wherein the risk factors associated with SZ include one or more of: a relative afflicted with schizophrenia, a genetically based phenotypic trait associated with risk for SZ; deficits in working memory; and mixed-handedness, particularly in females.

12. The method of claim 11, wherein the subject has one or more of a grandparent, parent, uncle or aunt, sibling, or child who has or had SZ.

13. The method of claim 11, wherein the genetically based phenotypic is eye tracking dysfunction.

14. The method of claim 1, wherein the subject is a child, fetus, or embryo, and one of the relatives of the subject has SZ.

15. The method of claim 1, further comprising administering a treatment to a subject identified as being at increased risk for developing SZ.

16. The method of claim 15, wherein the treatment is a pharmacological or psychosocial treatment for SZ.

17. The method of claim 1, further comprising using the information to select a subject population for a clinical trial.

18. The method of claim 1, further comprising using the information to stratify a subject population in a clinical trial.

19. The method of claim 1, further comprising using the information to stratify subjects that respond to a treatment from those who do not respond to a treatment, or subjects that have negative side effects from those who do not have negative side effects.

20. A method of selecting a human subject for inclusion or exclusion in a clinical trial, the method comprising:
   detecting the presence of a test haplotype in a sample from the subject, wherein the test haplotype comprises:
   (i) an A allele at rs138060;
   (ii) a C allele at rs138097; and
   (iii) a G allele at rs138110,
   obtaining a reference haplotype comprising reference markers that correspond to the polymorphisms; and
   comparing the test haplotype to the reference haplotype, wherein sharing of a haplotype between the test haplotype and a reference haplotype is indicative of whether there is an increased likelihood that the subject will develop schizophrenia (SZ);
   determining whether the subject has an increased risk of developing SZ based on the presence of a haplotype associated with an increased risk of developing SZ; and
   including or excluding the subject if the haplotype indicates that the subject has an increased risk of developing SZ.

21. The method of claim 20, wherein the clinical trial is of a treatment for SZ.

22. The method of claim 20, wherein the haplotype further includes an allele at microsatellite marker D22s1749e comprising more than 207 nucleotides.

\* \* \* \* \*

SEQUENCE LISTING

<160> NUMBER OF SEQ ID NOS: 4

<210> SEQ ID NO 1
<211> LENGTH: 25
<212> TYPE: DNA
<213> ORGANISM: Artificial Sequence
<220> FEATURE:
<223> OTHER INFORMATION: Primer

<400> SEQUENCE: 1
cagccgcacg ccatggaact cgaag                                              25

<210> SEQ ID NO 2
<211> LENGTH: 22
<212> TYPE: DNA
<213> ORGANISM: Artificial Sequence
<220> FEATURE:
<223> OTHER INFORMATION: Primer

<400> SEQUENCE: 2
ggcgccatga cgtcacgcct gc                                                 22

<210> SEQ ID NO 3
<211> LENGTH: 22
<212> TYPE: DNA
<213> ORGANISM: Artificial Sequence
<220> FEATURE:

-continued

```
<223> OTHER INFORMATION: Primer

<400> SEQUENCE: 3
agagcaagac tctgtctcaa ca                                              22

<210> SEQ ID NO 4
<211> LENGTH: 22
<212> TYPE: DNA
<213> ORGANISM: Artificial Sequence
<220> FEATURE:
<223> OTHER INFORMATION: Primer

<400> SEQUENCE: 4
ttctccttca ctttctgcca tg                                              22
```